US012290537B2

(12) United States Patent
Pagès Bosch et al.

(10) Patent No.: US 12,290,537 B2
(45) Date of Patent: May 6, 2025

(54) METHODS AND COMPOSITIONS FOR CONTROLLING OR REDUCING PESTS

(71) Applicants: HIPRA SCIENTIFIC, S.L.U., Amer (ES); UNIVERSIDAD PÚBLICA DE NAVARRA, Pamplona (ES)

(72) Inventors: Marc Pagès Bosch, Amer (ES); Primitivo Caballero Murillo, Pamplona (ES); Marta Sitjà I Arnau, Amer (ES); David Martínez Durán, Saragossa (ES); Javier Lucientes Curdi, Saragossa (ES)

(73) Assignees: HIPRA SCIENTIFIC, S.L.U., Amer (ES); UNIVERSIDAD PÚBLICA DE NAVARRA, Pamplona (ES)

( * ) Notice: Subject to any disclaimer, the term of this patent is extended or adjusted under 35 U.S.C. 154(b) by 509 days.

(21) Appl. No.: 17/630,450

(22) PCT Filed: Jul. 27, 2020

(86) PCT No.: PCT/EP2020/071144
§ 371 (c)(1),
(2) Date: Jan. 26, 2022

(87) PCT Pub. No.: WO2021/018841
PCT Pub. Date: Feb. 4, 2021

(65) Prior Publication Data
US 2022/0249577 A1 Aug. 11, 2022

(30) Foreign Application Priority Data
Jul. 26, 2019 (EP) .................................... 19382646

(51) Int. Cl.
*A61K 35/74* (2015.01)
*A01N 63/23* (2020.01)
*A01P 7/02* (2006.01)
*A61K 35/06* (2006.01)
*A61K 38/16* (2006.01)
*A61P 33/14* (2006.01)

(52) U.S. Cl.
CPC .............. *A61K 35/74* (2013.01); *A01N 63/23* (2020.01); *A01P 7/02* (2021.08); *A61K 35/06* (2013.01); *A61K 38/164* (2013.01); *A61P 33/14* (2018.01); *A61K 2300/00* (2013.01)

(58) Field of Classification Search
CPC ...... A61K 35/74; A61K 35/06; A61K 38/164; A61K 2300/00; A01N 63/23; A01P 7/02; A61P 33/14; C12R 2001/075; Y02A 50/30; C12N 1/205
See application file for complete search history.

(56) References Cited

U.S. PATENT DOCUMENTS

| | | | |
|---|---|---|---|
| 2006/0083726 | A1 | 4/2006 | Lysyk et al. |
| 2011/0027246 | A1 | 3/2011 | Tzeng et al. |
| 2015/0011389 | A1 | 1/2015 | Hellwege |
| 2016/0205945 | A1 | 7/2016 | Devisetty et al. |
| 2020/0360498 | A1 | 11/2020 | Foix Breto et al. |
| 2021/0077609 | A1 | 3/2021 | Grilló Dolset et al. |

FOREIGN PATENT DOCUMENTS

| | | |
|---|---|---|
| EP | 0 475 656 A2 | 3/1992 |
| EP | 0 932 682 A1 | 8/1999 |
| JP | H06507177 A | 8/1994 |
| JP | 2018507182 A | 3/2018 |
| WO | WO 9219106 A1 | 11/1992 |
| WO | 00/45641 A1 | 8/2000 |
| WO | 2006/096905 A1 | 9/2006 |
| WO | 2018/222063 A1 | 12/2018 |
| WO | WO 2019030529 A1 | 2/2019 |

OTHER PUBLICATIONS

Dunstand-Guzmán et al. Parasites & Vectors (2015) 8:285; DOI 10.1186/s13071-015-0890-6. (Year: 2015).*
Sparagano et al., Annu. Rev. Entomol. 2014. 59:447-66; 10.1146/annurev-ento-011613-162101. (Year: 2014).*
Schnepf et al., Microbiology and Molecular Biology Reviews, Sep. 1998, vol. 62, No. 3, p. 775-806. (Year: 1998).*
CN 101578278 A, 2009, English translation, 78 pages of PDF. (Year: 2009).*
Altschul et al., "Basic Local Alignment Search Tool," *Mol. Biol.* 215:403-410, May 15, 1990.
Ball et al., "The prevalence of pathogens in honey bee (*Apis mellifera*) colonies infested with the parasitic mite *Varroa jacobsoni*," *Ann. appl. Biol.* 113:237-244, Mar. 25, 1988.
Bradford, "A Rapid and Sensitive Method for the Quantitation of Microgram Quantities of Protein Utilizing the Principle of Protein-Dye Binding," *Anal. Biochem.* 72:248-254, Jan. 29, 1976.
Chauve et al., "The poultry red mite *Dermanyssus gallinae* (De Geer, 1778): current situation and future prospects for control," *Vet. Parasitol.* 79:239-245, Apr. 15, 1998.
Cosoroaba, "Massive Dermanyssus gallinae (De Geer 1778) invasion in battery-husbandry raised fowls in Romania [egg-laying decrease, mortality]," *Rev. Med. Vet.* 152(1):89-96, 2001. (with English Abstract).
Crickmore et al., "Revision of the Nomenclature for the *Bacillus thuringiensis* Pesticidal Crystal Proteins," *Microbiology and Molecular Biology Reviews* 62(3):807-813, Sep. 1998.
Crickmore, "*Bacillus thuringiensis* toxin nomenclature," 2016, URL= http://www.lifesci.sussex.ac.uk/home/Neil_Crickmore/Bt/, download date Jan. 25, 2022. (1 page).
Dean, "Biochemical Genetics of the Bacterial Insect-Control Agent *Bacillus thuringiensis*: Basic Principles and Prospects for Genetic Engineering," *Biotechnology and Genetic Engineering Reviews* 2:341-363, Oct. 1984.

(Continued)

*Primary Examiner* — Kade Ariani
(74) *Attorney, Agent, or Firm* — Seed IP Law Group LLP

(57) ABSTRACT

The present invention relates to methods and compositions comprising viable spores of *Bacillus thuringiensis* (Bt) strains for controlling or reducing mite infestations, such as the control and reduction of infestations produced by *Dermanyssus gallinae* (poultry red mite).

21 Claims, 3 Drawing Sheets

(56) References Cited

OTHER PUBLICATIONS

Figure 1:
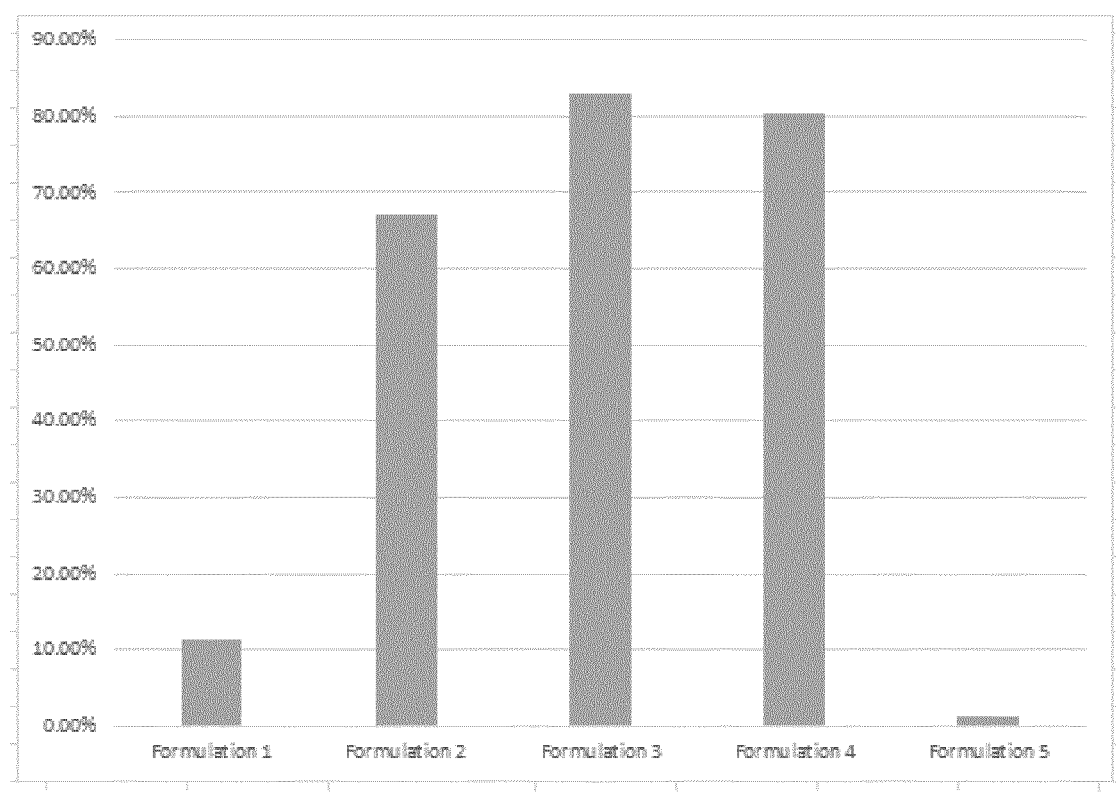

Goldman et al. (eds.), "Practical Handbook of Microbiology Third Edition," CRC Press, 2015, pp. 24-25.
Palma et al., "*Bacillus thuringiensis* Toxins: An Overview of Their Biocidal Activity," *Toxins* 6:3296-3325, Dec. 11, 2014.
Stewart et al., "Commitment of bacterial spores to germinate," *Biochem. J.* 198:101-106, Mar. 9, 1981.
Torres et al., "Actividad acaricida de *Bacillus thuringiensis* sobre el acaro rojo de las aves, *Dermanyssus gallinae*," *Rev. Vet* 29(2): 128-132, 2018. (with English Abstract).
Zhen et al., "Comparative Genomics of *Bacillus thuringiensis* Reveals a Path to Specialized Exploitation of Multiple Invertebrate Hosts," *mBio* 8(4):e00822-17, Aug. 8, 2017. (14 pages).

\* cited by examiner

METHODS AND COMPOSITIONS FOR CONTROLLING OR REDUCING PESTS

TECHNICAL FIELD OF THE INVENTION

The present invention relates to methods and compositions comprising viable spores of *Bacillus thuringiensis* (Bt) strains, preferably for veterinary use. The methods and compositions are for the prevention and treatment of mite infestations, particularly for controlling or reducing mite infestations produced by ectoparasites, such as the control and reduction of infestations produced by *Dermanyssus gallinae* (poultry red mite) which particularly affects avian species.

BACKGROUND OF THE INVENTION

Mites are small invertebrates, most of which are free living but some are parasitic. Mites that infest and parasitize animals cause infestations and/or infections, and huge losses in non-human animals. Mites are highly diverse and their classification is quite intricate. Mites and ticks, for example, are classed separately from insects (of the class Insecta). However, mites and ticks have a completely different biology between them.

Animal mites cause important types of skin diseases, and some mites infest other organs. Mites may infect different parts of the animal body such as the superficial layers of the skin, among the dead cells of the stratum corneum, e.g., *Psoroptes ovis*; the hair follicles of its hosts, e.g. *Demodex*; or they may infest their hosts whilst feeding for short periods, the so called bloodsuckling mites, e.g. *Dermanyssus gallinae*; other mites have adapted to infesting the lungs and air-sacs of birds or the lungs of mammals, e.g. Cytodites *nudus*; etc.

The ectoparasitic mite, *Varroa* destructor Anderson and Trueman (formerly called *Varroa jacobsoni* Oudemans), is a serious pest of the honey bee, *Apis mellifera* L. This haemolymph-feeding mite not only weakens adult and larval bees but also serves as a vector and inducer of viral infections in varroosis, causing severe damage to bee populations worldwide (Ball & Allen 1988). Another important pathological mite causing severe and worldwide infestation is the so called "red mite", "poultry red mite" or *Dermanyssus gallinae* (*D. gallinae*). The first source of concerns associated with red mite infestation is the extremely high and increasing prevalence of this disease in Europe. A recent epidemiological review reports that 83% of the European farms are infested by *D. gallinae*. This prevalence reaches 94% in The Netherlands, Germany and Belgium. Poultry red mite infestation affects all production types, from backyard or organic farms, to more intensive, enriched cage or barn systems. The impact of poultry red mite infestation has been increasing in Europe for the past decades and is expected to further increase.

One of the first factors contributing to this increase is the recent transformation of housing systems in laying hen husbandry in EU member countries. Directive 1999/74/EC on egg production and egg trade has banned the use of traditional cages for poultry birds since 2012. Although designed to improve the welfare of laying hens, this legislation has resulted in the move to housing systems incorporating more complex environments which appear to favor mite proliferation and exacerbate the problem of red mite infestation. For instance, enriched cages give far more hiding places for red mites to escape effective treatments. Mite infestation rates have been described to be much lower in hens kept in traditional cage systems compared to alternative ones. In 2009, before the first banning of conventional cages (Austria and Germany prohibited such cages from 2010 onwards), 74.4% of the laying hen housing systems still consisted in conventional cages in the European Union. In 2013, all member states had been able to complete the transformation process from conventional cages to mainly enriched cages, barn systems, and free range housing systems, meaning that within four years after 2009, the high majority of laying hens was transferred from a system unfavorable to mite proliferation to a system favoring it.

Another environmental factor expected to favor the proliferation of red mite infestation in the future is climate warming. During extreme weather events, red mite increased populations have been implicated in the deaths of large numbers of hens during the summer heat wave of 2003.

Finally, the removal of several chemical acaricide products from national markets due to safety concerns and the sustained lack of new effective control methods may have aggravated the *D. gallinae* prevalence in Europe. Therefore, there is a need to provide methods and compositions for controlling or reducing mite infestations, in particular for controlling or reducing mite infestations caused by *Dermanyssus gallinae* (poultry red mite).

In this sense, a review describing different possible strategies for the control of *D. gallinae* is described by Chauve C. et al., 1998, The poultry red mite *Dermanyssus gallinae* (De Geer, 1778): current situation and future prospects for control. Vet. Parasitol. 79 (1998) 239-248. According to Chauve et al., several *B. thuringiensis* strains have shown insecticide activity against lepidopterous and some dipterous pests. However, also according to this document, the use of *Bacillus thuringiensis* (*B. thuringiensis*) in vertebrates is compromised due to its toxicity at the cellular level.

*Bacillus thuringiensis* is an aerobic, spore-forming, gram-positive, and entomopathogenic bacterium. The species *B. thuringiensis* commonly consists of a large family of different subspecies which are categorized based on their phylogenetic and serotyping features (such as *B. thuringiensis* subsp. kurstaki, *B. thuringiensis* subsp. *aizawai*, etc.).

*B. thuringiensis* is well-known as a fast-acting and host-specific bio insecticide in agriculture.

The state of the art, see for example the recent review article Zhen et al., Comparative genomics of *Bacillus thuringiensis* reveals a path to specialized exploitation of multiple invertebrate hosts, American Society for Microbiology, 2017, 8(4), basically attributes the toxicity of *B. thuringiensis* to the different toxins produced by the bacteria, toxins which are described by the literature to play a major role in the targeting of insects and other invertebrates. Among said toxins insecticidal Cry proteins, vegetative insecticidal protein (Vip) toxins, and cytotoxin (Cyt) proteins are included.

The toxins identified in *B. thuringiensis* are continuously being updated. See e.g. www.lifesci.sussex.ac.uk/Home/Neil_Crickmore/Bt/. More than 900 toxin genes, encoding different entomopathogenic proteinaceous toxins, have been identified and characterized in *B. thuringiensis* strains isolated from different regions of the world.

In addition to the above toxins, *B. thuringiensis* produces other compounds, which also show a toxic effect, such as chitinase (an enzymatic protein), and metalloproteinase. *B. thuringiensis* also secretes other toxic compounds such as thuringiensin (Thu, beta-exotoxin or β-exotoxin), which is a thermostable secondary metabolite.

Torres, E. C. et al., 2018. Actividad acaricida de *Bacillus thuringiensis* sobre el ácaro rojo de las aves, *Dermanyssus gallinae*. Rev. Vet 29 (2): 128-132, 2018; evaluates the effect of *Bacillus thuringiensis* subspecies kurstaki (Btk) on larvae of poultry red mite by using a contact bioassay method. Torres et al., used the commercial product Dipel® in the study. According to Dipel®'s commercial label the insecticidal activity obtained by the use of said product is due to four proteins of *B. thuringiensis* subspecies kurstaki: Cry1Aa, Cry1Ab, Cry1Ac and Cry2 toxins produced by the subspecies kurstaki of *B. thuringiensis*. Based on the Cry, Cyt, and Vip protein contents, each strain may be specifically active towards insect plants such as lepidopteran, dipteran or coleopteran pests, and even other invertebrates, such as mites and nematodes, present both in plants and animals.

As already mentioned, the bioactivity of *B. thuringiensis* is thus mainly attributed to thuringiensin, and also to the parasporal crystalline proteins (or 5-endotoxins) Cry toxins. These Cry proteins are toxic to a wide variety of insect pest, such as Lepidoptera, Coleopteran and Dipteran species. The crystal is estimated to comprise about 30% of the total cellular protein of *B. thuringiensis* (Den D. H. et al., 1984).

Therefore, and as illustrated above, the literature is mainly focused on the toxicity of the previously mentioned toxins, particularly for the treatment of pests in agriculture.

However, the knowledge of the state of the art concerning the effect of *B. thuringiensis* on animal mites available is scarce. Very few in vitro and in vivo studies have reported the acaricidal activity of *B. thuringiensis* on animals, let alone the bioactivity of *B. thuringiensis* strains on animal mites.

At present, there is no authorized *B. thuringiensis* product for control of mite infestations in veterinary practice on the global market. Control remains dominated by the use of synthetic acaricides such as phoxim, abermectins, pyrethroids, amitraz, and other chemicals, where resistance issues and treatment failures have been widely reported. Therefore, safer and more efficacious control measures are needed for controlling mite infestations in animal production such as *D. gallinae* in poultry.

In conclusion, there is still a need in the art to find a solution to the problem of controlling mites, especially poultry mites, while not harming animals or humans. The use of environmental-friendly microbial miticides as substitutes for harmful chemical pesticides as an alternative for mass control of infestations/pests in non-human animals offers an advantageous and a new solution to that problem. In this regard, the present application shows for the first time that *B. thuringiensis* is suitable for the production of novel valuable miticide compositions and a promising alternative for the biocontrol of these types of infestations/pests in non-human animal production.

BRIEF DESCRIPTION OF THE FIGURES

FIG. 1 shows the mean mite mortality rate at 24 hours for the five different formulations illustrated in Example 1 (Formulations 1 to 5). The mean percentage of mite mortality at 24 hours is shown, as the ordinates, for the different formulations, as abscissas.

FIG. 2 shows the mean mite mortality rate at 24 hours and 48 hours for the three different formulations illustrated in Example 2 (Formulations 1 to 3). The mean percentage of mite mortality is shown as the ordinates, at 24 and 48 hours, for the different formulations, as the abscissas.

FIG. 3 shows the mean mite mortality rate at 24 hours and hours for the nine different groups illustrated in Example 3 (Groups 1 to 9). The mean percentage of mite mortality is shown, as the ordinates, at 24 and 48 hours for the nine different groups, as the abscissas.

FIG. 4 shows the mean mite mortality rate at 24 hours and 48 hours for the six different formulations illustrated in Example 5 (Formulations 1 to 6). The mean percentage of mite mortality is shown, as the ordinates, at 24 and 48 hours for the six different formulations, as the abscissas.

DESCRIPTION OF THE INVENTION

Definitions

Unless defined otherwise, all technical and scientific terms used herein have the same meaning as is commonly understood by one of skill in the art to which this invention belongs at the time of filing. However, in the event of any latent ambiguity, definitions provided herein take precedent over any other definition. Further, unless otherwise required by context, singular terms shall include pluralities and plural terms shall include the singular forms as well.

In this disclosure, "comprises," "comprising," "containing" and "having" and the like can have the meaning ascribed to them in European and U.S. patent law and can mean "includes," "including," and the like; "consisting essentially of" or "consists essentially" likewise has the meaning ascribed in European and U.S. patent law and the term is open-ended, allowing for the presence of more than that which is recited so long as basic or novel characteristics of that which is recited is not changed by the presence of more than that which is recited, but excludes prior art embodiments.

By "contacting" is meant touching, associating with, or having proximity to a composition. Such composition being applicable, without limitation, by bathing, spraying, pouring, painting, jetting, dipping and/or dusting.

By "controlling or reducing", "suitable for controlling or reducing", or "to control or reduce" of mite infestations is meant inhibiting or blocking mite survival or reducing, slowing, or stabilizing the growth of a mite population. In the context of this invention, mites can be all stages of the lifecycle that are known to the skilled person, such as juvenile development, larval stages and adult stages.

By "biological function" is meant any physiological or behavioral activity of an organism. Exemplary biological functions include, without limitation, reproduction, respiration, neural activity, locomotion.

By "an effective amount", is meant an amount effective that is required, either in a single dose or as part of a series to prevent or treat mite infestations of animals, i.e., to alleviate or reduce parasite numbers on an animal and/or its environment (such as cages, premises, fomites, etc.), and/or to inhibit the development of mite infections on an animal, in whole or in part, for example, by controlling and/or reducing mite population. The effective amount or effective dose is also able for controlling and/or reducing the severity of secondary infections or incident of disease in an animal for either the treatment or prevention of such disease. This amount will vary depending upon a variety of factors, including the physical condition of the subject, and can be readily determined by someone of skill in the art. At any rate, the effective amount can be preferably readily determined by observation or detection of the mites numbers on the animal and/or fomites, both before and after administering the compositions of the invention, e.g. the mite count is reduced after a first administration by 10% to 100%, preferably more than 50%, more preferably more than 70%, more preferably more than 80%, even more preferably more than 90%, even more preferably more than 95%, and even more preferably more than 99%. Factors affecting the effective amount may include, for example, the parasite species to be treated and the development stages of the parasites, the type (e.g., species and breed), age, size, sex, diet, activity and condition of the infested animals; the environment conditions such as temperature, humidity; thus, the preferred effective amount of the compositions according to this invention can vary.

By "infestation" is meant the colonization of a site or the parasitization of a live organism by a pest. The colonization of fomites (inanimate objects, that when contaminated with infectious agents, such as bacteria, viruses or parasites, can transfer disease to a new host) is also encompassed in the context of this invention. A pest is any living organism, whether animal, bacterial, parasite, virus, plant or fungus, which is invasive or troublesome to plants or animals, human or human concerns, livestock, or human structures. The animal groups of greatest importance as pests (in order of economic importance) are insects, mites, nematodes and gastropods. Such infestation may derive, in some occasions, in infection of the subject or host, exacerbating and/or worsening the health status, and/or causing a disease in such subject. There is a relationship between *D. gallinae* infestation and hen mortality (Cosoroaba I., 2001. Massive *Dermanyssus gallinae* invasion in battery-husbandry raised fowls. Rev. Med. Vet. Toulouse 152:89-96).

By "mites" is meant arachnid parasites that infest vertebrate and invertebrate animals such as mammals, fish, insects (for example bees) and avian species, particularly poultry animals. Examples of commercially important poultry mites, among others, are *Dermanyssus* sp, *Ornithonyssus* sp, Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates and Gaudoglyphus minor.

In the context of this invention, mites can be all stages of the lifecycle that are known to the skilled person, such as juvenile development, larval stages and adult stages.

By "*Dermanyssus gallinae*" is also understood "poultry red mite", also known as "chicken mite", "red mite" or "roost mite". It is a small ectoparasitic mite approximately 1.5 mm in length and varies in color from gray to brown/red depending on feeding status. Aside from the egg, poultry red mites have four life-cycle stages: larvae, protonymph, deutonymph and adult. Larvae hatch with six legs and do not feed. After the first molt, both nymphal stages and adults have eight legs. Protonymphs, deutonymphs and adult females routinely feed on host blood, but males only occasionally feed. Once on a host, red mites feed for short periods of up to an hour, doing so every two to four days and typically, although not exclusively, during periods of darkness. Complete development of *Dermanyssus gallinae*, from egg to adult through one larval stage and two nymphal stages, typically occurs over two weeks. *Dermanyssus gallinae* densities commonly reaches up to 50,000 mites per bird in caged systems, although densities can reach 500,000 mites per bird in severe cases. *D. gallinae* may be present year-round, but highest densities occur during hot and humid seasons. *D. gallinae* is found worldwide and is particularly serious in warmer regions of the temperate zone. It is an ectoparasitic mite that is considered temporary arthropod because they feed on, but do not permanently live on their host; but spend the majority of their adult live in the environment of such host. The mites stay on the host only to feed, and then move into neighboring cracks and crevices to lay eggs. The mites occur in both battery cages and floor systems. However, the problem is more common and widespread in floor and the "enriched" cage system that has been established in Europe due to animal welfare concerns; due to the presence of numerous suitable hiding places for the mites. The control of temporary parasites, such as *Dermanyssus gallinae*, is especially difficult because they can be both present on the host animal and in the environment.

By "miticide" is meant an agent that has miticidal activity, therefore, provoking deleterious effects over a biological function of a mite. The effect can be, e.g. ovicidal, larvicidal and/or adulticidal or a combination thereof.

By "miticidal activity" is meant any activity that inhibits, blocks, stops and/or reduces the growth, reproduction, or survival of a mite or other acaridae. The effect can be, e.g. ovicidal, larvicidal and/or adulticidal or a combination thereof.

By "preventing", "to prevent" or "prevention" of a mite infestation is meant, without limitation, decreasing, reducing or ameliorating the risk that a mite infestation will be established in a site, either by killing adult parasites and/or any development/larval stages, that are able to infest the host, before infestation of the host or, by killing or inhibiting the mites when they infest an animal that has been previously treated; or preventing generation of offspring of the mites, e.g. reducing the number of eggs laid and/or the hatching rate. Furthermore, it is meant preventing and/or protecting an animal for the adverse effects provoked by a pest, preferably by mite infestations. The effect can be e.g. ovicidal, larvicidal and/or adulticidal or a combination thereof. The effect can manifest itself directly, i.e. by killing the mites either immediately or after some times has elapsed for example by destroying their eggs, or indirectly, e.g., reducing the number of eggs laid and/or the hatching rate.

By "treating", "to treat" or "treatment" of a mite infestation" is meant, without limitation, restraining, limiting, reducing, stabilizing, or slowing the growth of a mite population in a site, either by killing adult parasites and/or any development/larval stages, that are able to infest the host, before infestation of the host or, by killing or inhibiting the mites when they infest an animal that has been previously treated. Furthermore, it is meant treating and protecting an animal for the adverse effects provoked by a pest, preferably by mite infestations, such as existing symptoms, clinical sings, disorders, conditions and/or diseases. The effect can be e.g. ovicidal, larvicidal and/or adulticidal or a combination thereof. The effect can manifest itself directly, i.e. by killing the mites either immediately or after some times has elapsed for example by destroying their eggs, or indirectly, e.g., reducing the number of eggs laid and/or the hatching rate.

By "medicament" or "medicinal product" is meant any pharmaceutical or veterinary composition (also referred to as medicine, medication, or simply drug) used to cure, treat or prevent disease in animals, including humans, as widely accepted. Drugs are classified in various ways. One key distinction is between traditional small-molecule drugs, usually derived from chemical synthesis, and biologicals or biopharmaceuticals, which, without limitation, include live or killed microorganisms, recombinant proteins, vaccines, blood products used therapeutically (such as IVIG), gene therapy, monoclonal antibodies and cell therapy (for instance, stem-cell therapies). In the present invention medicament preferably is a veterinary medicament, and even more preferably is a composition for veterinary use in animals and/or fomites.

By "pharmaceutical composition" is meant an active substance or combination of active substances intended to prepare a final medicinal product for prevention and/or therapeutic use. In the present invention the medicament or medicinal product preferably is a veterinary medicament, and even more preferably is a pharmaceutical composition for veterinary use. The pharmaceutical composition may be applied directly on the animals or indirectly in the environment where the animals are located.

By "Pharmaceutically acceptable" is meant a material that is not biologically or otherwise undesirable, i.e., the material can be administered to a subject along with the compositions of the invention without causing any undesirable biological effects or interacting in a deleterious manner with any of the components of such compositions. As used herein, the terms "pharmaceutically acceptable carrier" and "pharmaceutically acceptable vehicle" are interchangeable and refer to a vehicle for containing the active substances of a pharmaceutical composition that can be administered to a subject and/or the environment without adverse effects. Suitable pharmaceutically acceptable carriers include, but are not limited to, sterile water, purified water, saline, glucose, dextrose, or buffered solutions. Carriers may include auxiliary agents including, but not limited to, diluents, stabilizers, preservatives, wetting agents, dispersant agents, emulsifying agents, pH buffering agents (for example phosphate buffer), viscosity additives, and the like.

By "biocide composition" is meant a chemical substance, organism or microorganism intended to destroy, deter, render harmless, or exert a controlling effect on any harmful organism by chemical or biological terms. In the context of this invention, the biocide composition preferably refers to living organisms or compounds naturally produced by living organisms, such as microorganisms, preferably by bacterial microorganisms; and more preferably by *Bacillus thuringiensis*. The biocide composition may encompass diverse group of deleterious substances including insecticides, disinfectants, preservative and pesticides used for the control of live organisms that are harmful to human or animal health or that cause damage to natural or manufactured products. Biocidal products may contain one or more biocidal active substances and may contain other non-active co-formulants that ensure the effectiveness as well as the desired pH, viscosity, color, odor, etc. of the final biocide product. The biocide composition may be applied directly on the animals or indirectly in the environment where the animals are located.

By "bacterial preparation" is meant, as it is well known in the art, as a preparation comprising a bacterial culture, a part of a bacterial culture or a bacteria culture which has been post-treated. The bacterial preparation may comprise bacteria of one unique strain or more than one strain of the same bacteria. In the present invention, the bacterial preparation may comprise bacteria of one or more species of *Bacillus thuringiensis*, and subspecies thereof.

By "active ingredient" or "active substance" is meant the ingredient and/or substance in a pharmaceutical composition or biocide composition that is biologically active.

By "adjuvant" or "acceptable adjuvant" is understood, as is well known in the art, as non-nonspecific stimulants of the immune system which, administered together with the active substance, make the immunological response more effective. Some examples of adjuvants are: aluminum hydroxide, aluminum phosphate, aluminum oxide, muramyl dipeptides, vitamin E, squalane, squalene, *ginseng*, zymosan, glucans, dimethylaminoethyl-dextran, dextrans, non-ionic block polymers, monophosphoryl lipid A, vegetable oil, saponins, complete Freund's adjuvant, incomplete Freund's adjuvant, W/O, O/W, W/O/W type emulsions and mixtures thereof. It is also understood as components (such as stabilisers, preservatives and/or colouring agents) that are used to enhance the effectiveness and/or improve the ability to penetrate, target or protect the target organism of pesticides and/or biocides, such as herbicides, insecticides, fungicides, miticides, and other agents that control or eliminate unwanted pests.

By "Subject" means an individual. In one aspect, a subject is a mammal such as a primate, including humans. In another aspect, the mammal is a non-human primate such as marmosets, monkeys, chimpanzees, gorillas, orangutans and gibbons among others. The term "subject" also includes domesticated animals such as cats, dogs, etc.; livestock such as for example cattle, horses, pigs, sheep, goats, etc.; laboratory animals for example ferret, chinchilla, mouse, rabbit, rat, gerbil, guinea pig, etc.; and avian species such as chicken, turkeys, ducks, pheasants, pigeons, doves, parrots, cockatoos, geese, etc. Subjects can also include, but are not limited to fish (for example, zebrafish, goldfish, tilapia, salmon and trout), amphibians and reptiles. As used herein, a "subject" is the same as a "patient" or "host" or "affected subject", and the terms can be used interchangeably.

In the context of the present invention, the term "avian", "avian species", "avian subject" or "avian host" is understood to encompass all avian species prone or susceptible to mite infestation and/or infection, preferably by *D. gallinae* infection or infestation. The avian species encompassed by this invention include, for example, those collectively known as poultry or fowl animals. In other embodiments, these terms extend to include domesticated or game birds species such as, for example, chicken, turkeys, pheasants, geese and/or duck species. In one embodiment, the terms "avian", "avian species", "avian subject" or "avian host" extends to commercially important or farmed bird species, such as poultry.

By "laying hen" or "layer" is meant for adult female chickens (*Gallus domesticus*), that are primarily kept for laying eggs. Such eggs are generally used for consumption as human food. The term "laying hens" in this invention includes breeding stocks that are kept for producing eggs from which future laying hens hatch.

By "broiler" is meant gallinaceous domesticated fowl, bred and raised specifically for meat production.

By "premises where the animals are kept" is meant the place where the animals are permanently or temporary housed in such premises, have access to such premises either restricted in time (temporarily such as a stable for free ranging hens) or permanently such as conventional cages for laying hens or poultry houses for broilers.

In the context of the present invention, the term "non-spore proteins" or "non-sporal proteins" is referred to the set of proteins synthesized by vegetative *Bacillus thuringiensis* cells, that are not surrounded by the spore coat and generally also not by the exosporium; including among others, parasporal crystal proteins. The exosporium is the outer layer of mature spores and defines the boundary between the spore and the environment or host with which it interacts. For pathogens, that interaction includes the first point of contact of the spore with cells of the host's immune system. Although the crystal proteins are usually located outside the exosporium, there is a minority of cases, for some strains of *Bacillus thuringiensis*, that the exosporium may engulf the crystal proteins. Therefore, in the context of the present invention, the parasporal crystal proteins independently of their location, outside or inside the exosporium, are considered as non-spore proteins.

In the context of the present invention, the term "parasporal crystal proteins" is understood as the delta (δ)-endotoxins, proteins Cry and Cyt that are synthetized by vegetative *Bacillus thuringiensis* bacteria. This group of proteins aggregate, during the sporulation process, forming crystalline inclusions, known as crystals that are surrounded by a coat formed by the same protein type as the crystal but with different conformation. The crystalline protein or inclusion consists predominantly of a single or multiple polypeptides known as pro-toxins. The strains of the entomopathogenic *Bacillus thuringiensis* have the ability to form one or more crystalline inclusions, i.e., parasporal crystal proteins.

A full list of delta-endotoxins are available, for example, in Crickmore et al. 1998, 2016.

In the context of the present invention, the term "viable bacterial spores" is understood as *Bacillus thuringiensis* spores that have the ability to passively detect favorable environmental changes and germinate, producing vegetative cells that are physiologically active. On the contrary, the term "non-viable spore" refers to spores that are unable to germinate even when conditions are favorable. The number of viable bacterial spores may be determined by standard microbiological techniques such as the well-known Colony Forming Units per ml (CFU/ml) technique, which is based on viable cell counts (Goldman, Emanuel; Green, Lorrence H. Practical Handbook of Microbiology. 3rd Edition, published Jun. 4, 2015; Chapter 2. Quantification of Microorganisms. Page 19, Plate Count Method by Peter S. Lee, page 24. CRC Press, 1055 pages. ISBN 9781466587397). Counting colonies is usually performed manually using a pen and a click-counter. Alternatively, semi-automatic (software) and automatic (hardware+software) can be used.

In the context of the present invention, viable bacterial spores of *B. thuringiensis* (Bt) isolated from farms are preferred; more preferred are those Bt viable spores isolated from poultry farms; even more preferred are those Bt viable spores isolated from poultry farms with low or high degree of mite infestation; most preferred are those Bt viable spores isolated from poultry farms with low degree of mite infestation but with favorable conditions to finally result in high infestation rates of *Dermanyssus gallinae* mites.

In the context of the present invention, the term "non-crystalliferous" strain of *B. thuringiensis* means a strain with a genome (chromosome and plasmids DNA) with absence of Cry proteins. The absence of Cry proteins can be assessed by performing a DNA extraction from B. thurigiensis strain, using standard methods such as using InstaGene™ Matrix, a whole genome sequencing and subsequently checking in well-recognized genome databases (Crickmore et al., 1998, 2016) whether there exist any matches with Cry proteins. These databases contain complete Cry genes or genes with partial homology to Cry proteins. A non-crystalliferous strain of *B. thuringiensis* must have absence of Cry genes in any degree of homology to those genes (whole or partial sequence). Therefore, in a non-crystalliferous *B. thuringiensis* strain it is not possible to retrieve any results (complete or partial to described Cry proteins) from these databases.

Sequencing of the whole genome of strains of *B. thuringiensis* can be also performed using standard methods, such as Illumina HiSeq platform. Sequences can be assembled using software tools such as CLC Genomic Workbench (CLC Bio, Denmark). Reads are usually submitted to trimming to eliminate the extremes; low quality reads and reads with less than 30 base pairs. The resulting reads obtained are assembled the novo into contigs. The contigs obtained includes lectures of at least 95% of the aligned sequences paired with a reference sequence and with a percentage of identity of at least 95%. After the construction of contigs, the lectures are assigned to the contigs again. The obtained contigs are analyzed with BLAST (Altschul et al., 1990) using databases made of amino acid sequences of *Bacillus* (Crickmore et al., 1998, 2016). The BLAST is not restricted to the use of this database and may include other available databases known by the skilled man.

In the context of the present invention, the term "mutant protein" or "mutant toxin" is understood as the protein product encoded by a gene with non-silent mutation. Mutated protein can have single amino acid change (minor, but still in many cases significant change leading to disease) or wide-range amino acid changes by e.g. truncation of C-terminus after introducing premature stop codon.

DESCRIPTION

The authors of the present invention have surprisingly discovered that the activity of different *Bacillus thuringiensis* (Bt) strains on the mortality of mites, such as *D. gallinae* mites, is predominantly linked to the presence of an effective amount of bacterial viable spores and not to the presence of non-spore proteins such as parasporal crystal proteins and/or other toxins produced by said Bt strains. As far as we know, this is the first time that such activity is clearly linked to viable bacterial spores and not predominantly linked with respect to the non-spore proteins such as parasporal crystal proteins produced by said Bt strains.

Experimental evidence supporting the present findings can be found through-out the examples of the specification. In this sense, example 1 shows that the non-crystalliferous strain of *B. thuringiensis* (GR-S5-8) deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen and Zellkulturen (Inhoffenstraße 7B, 38124 Braunschweig, Germany) under the accession number DSM 33175 on Jun. 20th, 2019, which does not produce parasporal crystal proteins at all, provided a 83% mortality rate (Formulation 3) higher than those formulations containing both, spores and parasporal crystal proteins (Formulation 2). Furthermore, in this example, it was further observed that the experimental formulation 4 which was enriched with purified viable spores, resulted in an increase of activity over other formulations, causing a higher reduction of *D. gallinae* population (80% of mite mortality), when compared to non-purified formulation 2 that contained both, spores and parasporal crystal proteins, the later resulting in 67% of mite mortality. It was certainly unexpected that a purified formulation enriched with viable spores had a better activity on mortality against mites than that observed in compositions containing parasporal crystal proteins. In addition, when the viable spores and parasporal crystal proteins were subjected to an inactivation by heat-treatment, no mite mortality was observed (Formulation 5) at all; that is to say, parasporal crystal proteins without the presence of viable spores do not show activity against mites. To the inventors' best knowledge, this is the first time that anti-mite activity, such as anti *D. gallinae* activity, is clearly linked to viable Bt spores instead of to the presence of non-spore proteins such as parasporal crystal proteins produced by Bt strains.

Furthermore, as shown in example 3, it was further observed that the less viable spores are present in the composition, the less mortality rate of *D. gallinae* mites, both at 24 and 48 hours post-treatment with the experimental formulations. Likewise, the higher the dose of viable spores, the higher the mortality was, irrespectively of the content of non-spore proteins of the composition. These results further demonstrate the role of the viable spores for producing anti-mite activity. Likewise, all the tested Bt strains had a significant mortality when formulated at $3.1 \times 10^9$ viable spores (CFU)/ml. In particular, the deposited DSM 33035 Bt strain, DE2-S2-8, demonstrated a higher degree of anti-mite activity, showing a mortality rate of 66% at 48 hours post-treatment (Group 9).

Moreover, unexpectedly, the mixture of the *B. thuringiensis* preparations with mineral oil did not have a negative impact on the viability of *B. thuringiensis* strains and their anti-mite activity. On the contrary, it considerably increased the effect of the experimental formulations resulting in a synergic effect on mite mortality. In this sense, and as shown in example 5, formulation 3 prepared with mineral oil and $3.1 \times 10^9$ viable spores (CFU)/ml (Group 3) achieved a mite mortality rate over 90% in just 48 hours. It was further observed that the mixture of the *B. thuringiensis* formulations blended in mineral oil preparations, allowed reducing the dose of *B. thuringiensis* bacteria used in the experimental formulations. For instance, mineral oil preparation formulated with a dose of $3.4 \times 10^8$ viable spores (CFU)/ml (Group 1) resulted in a mite mortality rate of 70.10% at 48 hours. Similar mortality rate was obtained when the *B. thuringiensis* formulation was not mixed with mineral oil but in this case it was formulated at a dose of $3.1 \times 10^9$ viable spores (CFU)/ml (Group 5), i.e. much higher dose was needed to achieve a similar result on mortality rate (68%) without the presence of mineral oil in the experimental formulations.

Thus, the synergistic effect of Bt preparations plus mineral oil was confirmed. In additional experiments, it was also observed that mixing a FS Bt sample with an emulsion comprising very low percentages of mineral oil, such as 1.25% a synergistic effect was still maintained.

In virtue of the results provided thus far, a first aspect of the invention refers to a pharmaceutical or biocide composition suitable for controlling or reducing mite infestations, comprising as an active ingredient a bacterial preparation of at least one strain of *Bacillus thuringiensis* (*B. thuringiensis*), characterized in that the bacterial preparation comprises an effective amount of viable spores of at least said one strain of *B. thuringiensis*. Preferably, the bacterial preparation comprises an effective amount of at least $1 \times 10^4$ cfu of viable spores per ml of the composition, preferably at least $1 \times 10^5$ cfu of viable spores per ml of the composition, preferably at least $1 \times 10^6$ cfu of viable spores per ml of the composition, also preferably at least $1 \times 10^7$ cfu of viable spores per ml of the composition. More preferably, the bacterial preparation comprises an effective amount of at least $3 \times 10^8$ cfu of viable spores per ml of the composition. Still more preferably, the bacterial preparation comprises an effective amount of at least $3 \times 10^9$ cfu of viable spores per ml of the composition.

In a preferred embodiment of the first aspect of the invention or of any of its preferred embodiments, the bacterial preparation comprises an effective amount of a purified formulation enriched with viable spores of at least one strain of *Bacillus thuringiensis* (*B. thuringiensis*). It is noted that such purified population could comprise any of the strains identified throughout the present invention including *Bacillus thuringiensis* subspecies kurstaki (Btk). In particular, the purified population of viable spores contains a significantly higher proportion of viable spores than the crude population of bacteria from which the viable spores are isolated. For example, the purification procedure should lead at least to a five-fold increase, preferably at least a ten-fold increase, more preferably at least a fifteen-fold increase, most preferably at least a twenty-fold increase, and optimally at least a twenty-five fold increase in viable spores with respect to the crude population.

Accordingly, the purified populations of the invention contain significantly higher levels of viable spores than those that exist in nature, as described above.

In another preferred embodiment of the first aspect of the invention or of any of its preferred embodiments, the bacterial preparation comprises an effective amount of viable spores of at least one strain of *B. thuringiensis* suitable for controlling or reducing mite infestations produced by *Dermanyssus gallinae* (poultry red mite).

In another preferred embodiment of the first aspect of the invention or of any of its preferred embodiments, the at least one strain of *B. thuringiensis* is a strain that, is preferably suitable for controlling or reducing mite infestations produced by *Dermanyssus gallinae* (poultry red mite), and produces less amount of non-spore proteins such as parasporal crystal proteins than viable spores per ml of composition. Preferably, the at least one strain of *B. thuringiensis* is a strain that, is preferably suitable for controlling or reducing mite infestations produced by *Dermanyssus gallinae* (poultry red mite), and produces less amount of non-spore proteins such as parasporal crystal proteins than *Bacillus thuringiensis* subspecies kurstaki (Btk), subspecies aizawai, subsepcies israelensis and subspecies morrisoni. More preferably, the at least one strain of *B. thuringiensis* is a strain that, is preferably suitable for controlling or reducing mite infestations produced by *Dermanyssus gallinae* (poultry red mite), and produces less *B. thuringiensis* non-spore proteins such as parasporal crystal proteins for every $3.1 \times 10^9$ viable spores per ml than the naturally occurring microorganism *Bacillus thuringiensis* subspecies kurstaki (Btk). Still more preferably, the at least one strain of *B. thuringiensis* is a strain that, is preferably suitable for controlling or reducing mite infestations produced by *Dermanyssus gallinae* (poultry red mite), and produces less than 1.7 mg/ml of *B. thuringiensis* non-spore proteins such as parasporal crystal proteins for every $3.1 \times 10^9$ viable spores per ml, preferably less than 1.5 mg/ml of *B. thuringiensis* non-spore proteins such as parasporal crystal proteins for every $3.1 \times 10^9$ viable spores per ml, or less than 1.3 mg/ml of *B. thuringiensis* non-spore proteins such as parasporal crystal proteins for every $3.1 \times 10^9$ viable spores per ml, or less than 0.8 mg/ml of *B. thuringiensis* non-spore proteins such as parasporal crystal proteins for every $3.1 \times 10^9$ viable spores per ml, or less than 0.5 mg/ml of *B. thuringiensis* non-spore proteins such as parasporal crystal proteins for every $3.1 \times 10^9$ viable spores per ml, or less than 0.3 mg/ml of *B. thuringiensis* non-spore proteins such as parasporal crystal proteins for every $3.1 \times 10^9$ viable spores per ml, or less than 0.1 mg/ml of *B. thuringiensis* non-spore proteins such as parasporal crystal proteins for every $3.1 \times 10^9$ viable spores per ml.

Still more preferably, the *B. thuringiensis*' non-spore proteins such as parasporal crystal proteins indicated in the above paragraph are selected from the list consisting of: delta (8)-endotoxins, such as the proteins Cry and Cyt that are synthetized by the vegetative *Bacillus thuringiensis* bacteria. These group of proteins aggregate, during the sporulation process, forming crystalline inclusions, known as crystals that are surrounded by a coat formed by the same protein type as the crystal but with different conformation. A non-limiting non-spore proteins selection are delta (8)- endotoxins such as Cry (Cry1, Cry2, Cry3, etc.) and Cyt (Cyt1, Cyt3, etc.) family proteins (Crickmore et al., 1998, 2016); vegetative insecticidal proteins such as Vip family proteins (Vip1, Vip2, Vip3 and Vip4); secreted insecticidal proteins such as Sip family proteins; β-exotoxins such as thuringiensin, proteins related to cholesterol-dependent cytolysins such as sphaericolysins and alveolysins; Enhancing-like proteins such as Bel enhancing; Helper proteins such as P19 and P20 proteins, or non-proteinaceous β-exotoxin such as the Bt 41.9-kDa protein (Palma et al., 2014. *Bacillus thuringiensis* Toxins: An Overview of Their Biocidal Activity. Toxins 2014, 6, 3296-3325; doi: 10.3390/toxins6123296).

In another preferred embodiment of the first aspect of the invention or of any of its preferred embodiments, the at least one strain of *Bacillus thuringiensis*, is selected from the list consisting of:
- the *Bacillus thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33175 on Jun. 20, 2019, respectively, and mutants thereof;
- *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33034 on Feb. 21, 2019, respectively, and mutants thereof; and
- *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33035 on Feb. 21, 2019, respectively, and mutants thereof.

In another preferred embodiment of the first aspect of the invention or of any of its preferred embodiments, the pharmaceutical or biocide composition further comprises at least one further active or functional ingredient selected from the group consisting of: an insecticide, an acaricide, a fungicide, a nematicide, an antibiotic, a cleaning agent, an immunogenic agent, animal feedstuff, an essential oil, a mineral oil, a nutraceutical, a probiotic, a prebiotic, a symbiotic, a polysaccharide, and combinations thereof. Preferably, the further active ingredient is an immunogenic agent derived from a microorganism selected from the group consisting of avian infectious bronchitis virus (IBv), newcastle disease virus (NDV), Adenovirus, egg drop syndrome virus (EDS), infectious bursal disease virus (IBDV), chicken anemia virus, avian encephalo-myelitis virus, fowl pox virus, turkey rhinotracheitis virus, duck plague virus, pigeon pox virus, marek disease virus (MDV), avian leucosis virus, infectious laryngotracheitis virus (ILTV), avian pneumovirus, reovirus, *Escherichia coli, Salmonella* sp., *Ornithobacterium rhinotracheale, Haemophilus paragallinarum, Pasteurella multocida, Erysipelothrix rhusiopathiae*, Erysipela sp., *Mycoplasma* sp., *Clostridium* sp., *Eimeria* sp., and *Aspergillus* sp.

In another preferred embodiment of the first aspect of the invention or of any of its preferred embodiments, the pharmaceutical or biocide composition is in the pharmaceutical form selected from the group consisting of: dust, powder, granular formulation, microencapsulated formulation, lotion, ointment, gel, cream, paste, suspension, liquid concentrate, solution and emulsion. Preferably, the pharmaceutical or biocide composition is suitable for application by bathing, spraying, pouring, painting, jetting, dipping or dusting.

In yet another preferred embodiment of the first aspect of the invention or of any of its preferred embodiments, the composition further comprises one or more pharmaceutically acceptable vehicles and/or one or more acceptable adjuvants.

A second aspect of the present invention refers to the pharmaceutical or biocide composition as defined in the first aspect of the invention or in any of its preferred embodiments, for use as a medicament or as a biocide.

A third aspect of the present invention refers to the pharmaceutical or biocide composition as defined in the first aspect of the invention or in any of its preferred embodiments, for use in the control and/or reduction of mite infestations.

A fourth aspect of the present invention refers to the pharmaceutical or biocide composition as defined in the first aspect of the invention or in any of its preferred embodiments, for use in the control and/or reduction of mite infestations produced by ectoparasite mites, preferably in animals or fomites. Preferably wherein the ectoparasite mite is selected from the group consisting of: *Dermanyssus* sp, *Ornithonyssus* sp, *Argus* sp, Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus minor, Otodectes *cynotis, Cheyletiella yasguri, Demodex* sp., Notoederes *cati, Cheyletiella* sp., *Psoroptes* sp., Chorioptes sp., Psorergates *ovis, Sarcoptes scabiei, Psorobia ovis*, Raillietia *auris* and *Varroa* sp., and combinations thereof. More preferably, wherein the ectoparasite mite is *Dermanyssus gallinae* (poultry red mite).

In a preferred embodiment of the fourth aspect of the invention, the animals are selected from the group consisting of avian, porcine, bovine, equine, feline, canine, ovine, rabbit and honeybees species. Preferably, the avian species are poultry.

In another preferred embodiment of the fourth aspect of the invention or of any of its preferred embodiment, the ectoparasite mite is selected so that the control and/or reduction of mite infestation results in a mortality rate of at least 25% of the mites; preferably, wherein the mortality rate of at least 25% of the mites results in 48 hours from the moment in which the composition has been applied onto and/or has contacted with said mites and/or fomites. In another preferred embodiment of the fourth aspect of the invention, the ectoparasite mite is selected so that the control and/or reduction of mite infestation results in a mortality rate of at least 40% of the mites; preferably, wherein the mortality rate of at least 40% of the mites results in 48 hours from the moment in which the composition has been applied onto and/or has contacted with said mites and/or fomites. In another preferred embodiment of the fourth aspect of the invention, the ectoparasite mite is selected so that the control and/or reduction of mite infestation results in a mortality rate of at least 50% of the mites; preferably, wherein the mortality rate of at least 50% of the mites results in 48 hours from the moment in which the composition has been applied onto and/or has contacted with said mites and/or fomites. In another preferred embodiment of the fourth aspect of the invention, the ectoparasite mite is selected so that the control and/or reduction of mite infestation results in a mortality rate of at least 60% of the mites; preferably, wherein the mortality rate of at least 60% of the mites results in 48 hours from the moment in which the composition has been applied onto and/or has contacted with said mites and/or fomites. In another preferred embodiment of the fourth aspect of the invention, the ectoparasite mite is selected so that the control and/or reduction of mite infestation results in a mortality rate of at least 70% of the mites; preferably, wherein the mortality rate of at least 70% of the mites results in 48 hours from the moment in which the composition has been applied onto and/or has contacted with said mites and/or fomites.

In yet another preferred embodiment of the fourth aspect of the invention or of any of its preferred embodiments, the pharmaceutical or biocide composition is applied by bathing, spraying, pouring, painting, jetting, dipping or dusting.

In another preferred embodiment of the fourth aspect of the invention or of any of its preferred embodiments, the at least one strain of *Bacillus thuringiensis*, is selected from the list consisting of:

the *Bacillus thuringiensis* (Bt) strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33175 on Jun. 20, 2019, respectively, and mutants thereof;

*B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33034 on Feb. 21, 2019, respectively, and mutants thereof; and

*B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen and Zellkulturen (Inhoffenstraße 7B, 38124 Braunschweig, Germany) under the accession numbers DSM 33035 on Feb. 21, 2019, respectively, and mutants thereof.

A fifth aspect of the invention refers to a method for the control and/or reduction of mite infestations in fomites, wherein the method comprises using the pharmaceutical or biocide composition as defined in the first aspect of the invention or in any of its preferred embodiments, preferably wherein the fomites are located in premises where animals are kept; more preferably wherein the animals are selected from the group consisting of avian, porcine, bovine, equine, feline, canine, ovine, rabbit and honeybees species.

In a preferred embodiment of the fifth aspect of the invention or of any of its preferred embodiment, the ectoparasite mite is selected so that the control and/or reduction of mite infestation results in a mortality rate of at least 25% of the mites; preferably, wherein the mortality rate of at least 25% of the mites results in 48 hours from the moment in which the composition has been applied onto and/or has contacted with said mites and/or fomites. In another preferred embodiment of the fifth aspect of the invention, the ectoparasite mite is selected so that the control and/or reduction of mite infestation results in a mortality rate of at least 40% of the mites; preferably, wherein the mortality rate of at least 40% of the mites results in 48 hours from the moment in which the composition has been applied onto and/or has contacted with said mites and/or fomites. In another preferred embodiment of the fifth aspect of the invention, the ectoparasite mite is selected so that the control and/or reduction of mite infestation results in a mortality rate of at least 50% of the mites; preferably, wherein the mortality rate of at least 50% of the mites results in 48 hours from the moment in which the composition has been applied onto and/or has contacted with said mites and/or fomites. In another preferred embodiment of the fifth aspect of the invention, the ectoparasite mite is selected so that the control and/or reduction of mite infestation results in a mortality rate of at least 60% of the mites; preferably, wherein the mortality rate of at least 60% of the mites results in 48 hours from the moment in which the composition has been applied onto and/or has contacted with said mites and/or fomites. In another preferred embodiment of the fifth aspect of the invention, the ectoparasite mite is selected so that the control and/or reduction of mite infestation results in a mortality rate of at least 70% of the mites; preferably, wherein the mortality rate of at least 70% of the mites results in 48 hours from the moment in which the composition has been applied onto and/or has contacted with said mites and/or fomites. In another preferred embodiment of the fifth aspect of the invention or of any of its preferred embodiments, the pharmaceutical composition or biocide composition is applied in fomites which are located in premises where the animals are kept.

In yet another preferred embodiment of the fifth aspect of the invention or of any of its preferred embodiments, the pharmaceutical or biocide composition is applied by bathing, spraying, pouring, painting, jetting, dipping or dusting.

In another preferred embodiment of the fifth aspect of the invention or of any of its preferred embodiments, the at least one strain of *Bacillus thuringiensis*, is selected from the list consisting of:

the *Bacillus thuringiensis* (Bt) strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33175 on Jun. 20, 2019, respectively, and mutants thereof;

*B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33034 on Feb. 21, 2019, respectively, and mutants thereof; and

*B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33035 on Feb. 21, 2019, respectively, and mutants thereof.

In a sixth aspect of the invention, the pharmaceutical or biocide composition as defined in the first aspect of the invention or in any of its preferred embodiments, comprises a further active ingredient and said further active ingredient is an essential oil or a mineral oil. Preferably, said composition is formulated in said essential oil or mineral oil. More preferably, the further active ingredient is a mineral oil and said mineral oil is liquid paraffin.

A seventh aspect of the invention refers to a pharmaceutical or biocide composition as defined in the sixth aspect of the invention, for use in the control and/or reduction of mite infestations, preferably in animals or fomites. Preferably, the control and/or reduction of mite infestations is performed in fomites, wherein the fomites are preferably located in premises where the animals are kept. Also preferably, the control and/or reduction of mite infestations is performed in animals, wherein the animals are selected from the group consisting of avian, porcine, bovine, equine, feline, canine, ovine, rabbit and honeybees species. Preferably, the avian species are poultry.

In a preferred embodiment of the seventh aspect of the invention or of any of its preferred embodiment, the ectoparasite mite is selected so that the control and/or reduction of mite infestation results in a mortality rate of at least 25% of the mites; preferably, wherein the mortality rate of at least 25% of the mites results in 48 hours from the moment in which the composition has been applied onto and/or has contacted with said mites and/or fomites. In another preferred embodiment of the seventh aspect of the invention, the ectoparasite mite is selected so that the control and/or reduction of mite infestation results in a mortality rate of at least 40% of the mites; preferably, wherein the mortality rate of at least 40% of the mites results in 48 hours from the moment in which the composition has been applied onto and/or has contacted with said mites and/or fomites. In another preferred embodiment of the seventh aspect of the invention, the ectoparasite mite is selected so that the control and/or reduction of mite infestation results in a mortality rate of at least 50% of the mites; preferably, wherein the mortality rate of at least 50% of the mites results in 48 hours from the moment in which the composition has been applied onto and/or has contacted with said mites and/or fomites. In another preferred embodiment of the seventh aspect of the invention, the ectoparasite mite is selected so that the control and/or reduction of mite infestation results in a mortality rate of at least 60% of the mites; preferably, wherein the mortality rate of at least 60% of the mites results in 48 hours from the moment in which the composition has been applied onto and/or has contacted with said mites and/or fomites. In another preferred embodiment of the seventh aspect of the invention, the ectoparasite mite is selected so that the control and/or reduction of mite infestation results in a mortality rate of at least 70% of the mites; preferably, wherein the mortality rate of at least 70% of the mites results in 48 hours from the moment in which the composition has been applied onto and/or has contacted with said mites and/or fomites. In another preferred embodiment of the seventh aspect of the invention, the ectoparasite mite is selected so that the control and/or reduction of mite infestation results in a mortality rate of at least 80% of the mites; preferably, wherein the mortality rate of at least 80% of the mites results in 48 hours from the moment in which the composition has been applied onto and/or has contacted with said mites and/or fomites. In another preferred embodiment of the seventh aspect of the invention, the ectoparasite mite is selected so that the control and/or reduction of mite infestation results in a mortality rate of at least 90% of the mites; preferably, wherein the mortality rate of at least 90% of the mites results in 48 hours from the moment in which the composition has been applied onto and/or has contacted with said mites and/or fomites.

In an alternative embodiment of the seventh aspect of the invention, the invention refers to the pharmaceutical or biocide composition as defined in the first or sixth aspects of the invention, for use in the prevention and/or treatment of a disease caused by ectoparasite mites in an animal in need thereof. Preferably, the disease is caused by an ectoparasite mite selected from the group consisting of *Dermanyssus* sp., *Ornithonyssus* sp., *Argus* sp., Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus minor, Otodectes *cynotis, Cheyletiella yasguri, Demodex* sp., Notoederes *cati*, Cheyletella sp., *Psoroptes* sp., Chorioptes sp., Psorergates *ovis, Sarcoptes scabiei, Psorobia ovis*, Raillietia *auris* and *Varroa* sp., and combinations thereof. Also preferably, the prevention and/or treatment of mite infestations is performed in animals, wherein the animals are selected from the group consisting of avian, porcine, bovine, equine, feline, canine, ovine, rabbit and honeybees species. Preferably, the avian species are poultry.

In yet another preferred embodiment of the seventh aspect of the invention or of any of its preferred embodiments, the pharmaceutical or biocide composition is applied by bathing, spraying, pouring, painting, jetting, dipping or dusting.

In another preferred embodiment of the seventh aspect of the invention or of any of its preferred embodiments, the at least one strain of *Bacillus thuringiensis*, is selected from the list consisting of:

the *Bacillus thuringiensis* (Bt) strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33175 on Jun. 20, 2019, respectively, and mutants thereof;

*B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33034 on Feb. 21, 2019, respectively, and mutants thereof; and

*B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33035 on Feb. 21, 2019, respectively, and mutants thereof.

In another preferred embodiment of the seventh aspect of the invention or of any of its preferred embodiments, the mite is an ectoparasite mite. Preferably, the ectoparasite mite is selected from the group consisting of *Dermanyssus* sp, *Ornithonyssus* sp, *Argus* sp, Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus *minor*, Otodectes *cynotis, Cheyletiella yasguri, Demodex* sp., Notoederes *cati*, Cheyletiella sp., *Psoroptes* sp., Chorioptes sp., Psorergates *ovis, Sarcoptes scabiei, Psorobia ovis*, Raillietia *auris* and *Varroa* sp. More preferably, the ectoparasite mite is *Dermanyssus gallinae* (poultry red mite).

In yet another preferred embodiment of the seventh aspect of the invention or of any of its preferred embodiments, the composition is applied by bathing, spraying, pouring, painting, jetting, dipping or dusting. Preferably, the composition is applied by spraying.

The present invention is further shown in light of the following examples which merely illustrate the invention but do not limit the same. Furthermore, the present invention covers all possible combinations of particular and preferred embodiments described herein.

EXAMPLES

Example 1: Spore Activity Assessment. Bioassay by Ingestion

The goal of the present example was to study the activity of different *Bacillus thuringiensis* (Bt) strains which were also formulated in different conditions, against *Dermanyssus gallinae* mites using a bioassay performed by ingestion.

*Bacillus thuringiensis* (Bt) DSM 33173 strain (strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession number DSM 33173 on Jun. 20, 2019) and *B. thuringiensis* DSM 33175 strain (strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession number DSM 33175 on Jun. 20, 2019), isolated from Spain were used in this assay. Strain DSM 33175 was specifically isolated from a poultry farm where a high infestation rate of *D. gallinae* were recorded. DSM 33175 strain is a Bt strain which does not have genes coding for parasporal crystal proteins. Therefore, one of the strains included in the activity bioassay was a non-crystalliferous Bt strain, in particular the DSM 33175 strain. On the other hand, DSM 33173 Bt strain was characterized as a strain containing both, spores and parasporal crystal proteins (Cry21 and Cry55 genes were detected once the genome of the Bt DSM 33173 strain was sequenced using standard methods).

In order to determine whether a Bt strain is a non-crystalliferous strain, the skilled man can use general common knowledge. As it is well-known, a non-crystalliferous strain of *B. thuringiensis* is a strain with a genome (chromosome and plasmids DNA) with absence of Cry proteins. The absence of Cry proteins can be assessed by performing a DNA extraction from B. thurigiensis strain, using standard methods such as using InstaGene™ Matrix, a whole genome sequencing and subsequently checking in well-recognized genome databases (Crickmore et al., 1998, 2016) whether there exist any matches with Cry proteins. These databases contain complete Cry genes or genes with partial homology to Cry proteins. A non-crystalliferous strain of *B. thuringiensis* must have absence of Cry genes in any degree of homology to those genes. Therefore, in a non-crystalliferous *B. thuringiensis* strain it is not possible to retrieve any results (complete or partial to described Cry proteins) from these databases.

Sequencing of the whole genome of strains of *B. thuringiensis* can be also performed using standard methods, such as Illumina HiSeq platform. Sequences can be assembled using software tools such as CLC Genomic Workbench (CLC Bio, Denmark). Reads are usually submitted to trimming to eliminate the extremes; low quality reads and reads with less than 30 base pairs. The resulting reads obtained are assembled the novo into contigs. The contigs obtained includes lectures of at least 95% of the aligned sequences paired with a reference sequence and with a percentage of identity of at least 95%. After the construction of contigs, the lectures are assigned to the contigs again. The obtained contigs are analyzed with BLAST (Altschul et al., 1990) using databases made of amino acid sequences of *Bacillus* thuringiensis toxins (Crickmore et al., 1998, 2016). The BLAST is not restricted to the use of this database and may include other available databases known by the skilled man.

In the present example, an individual colony of both strains, DSM 33173 and DSM 33175, was inoculated in different Erlenmeyers as follows. The colony was cultured in an Erlenmeyer of 250 ml with 80 ml CCY Medium (Stewart, G. S. A., K. Johnstone, E. Hagelberg, and D. J. Ellar. 1981. Commitment of bacterial spores to germinate. Biochem. J. 198:101-106) at 28° C. for 72 hours in an incubator shaker under agitation at 220 rpm. At 72 hours, spores formation was checked by visual inspection using an optic microscope at 1,000× and it was confirmed that they were fully formed. At this point, 1 M of NaCl and 10 mM EDTA was added to the culture. After that, the culture was centrifuged at 11,200 G for 10 minutes at 4° C. The pellet was subsequently re-suspended with Mili-Q water and the supernatant discarded. The re-suspended pellet was centrifuged at 11,200 G for 10 minutes at 4° C. for a second time. The supernatant was discarded once again and the pellet was re-suspended with Mili-Q water. The re-suspended pellet was centrifuged at 11,200 G for 10 minutes at 4° C. for third time, the resulting supernatant was discarded once again and the pellet was finally re-suspended with Mili-Q water up to a final volume of 1.5-1.8 ml to obtain a final suspension of Bt sample for the bioassay (It was named FS Bt sample).

The content on non-spore proteins contained in the final suspension of the Bt sample was then quantified. In order to perform this quantification, the FS Bt sample was diluted ¹/₁₀ with purified water and then homogenized. After that, 940 ml of carbonate buffer at pH 11.3, 10 µl of dithiothreitol (DTT) 1 M and 50 µl of the ¹/₁₀ diluted FS Bt sample suspension were added to a 1.5 ml Eppendorf tube. Then, the Eppendorf tube was incubated at 37° C. for 2 hours in an incubator shaker under agitation at 220 rpm. At this point, the Eppendorf tube was centrifuged at 13,200 G for 5 minutes. Finally, the supernatant was used to quantify the non-spore proteins. The quantification was done by standard techniques for protein quantification such as the Bradford protein assay described in Bradford, M. M. 1976. A rapid and sensitive method for the quantitation of microgram quantities of protein utilizing the principle of protein-dye binding. Anal. Biochem. 72:248-254.

In order to perform the ingestion bioassay the following solution was previously prepared: 10 ml Fetal Bovine Serum (FBS) homogenate, 50 mg of D-glucose, 25 mg of ATP and 100 µl of a coloring solution (35 g/l Quinoline yellow E-104, 40 g/l Patent blue E-131 in PBS until 50 ml), which was labelled as FBS final solution.

Five different experimental formulations were subsequently prepared using that FBS final solution:

Formulation 1: Negative Control:FBS final solution mixed 1:1 (v/v) with same volume of purified water.

Formulation 2 (Bt DSM 33173): FBS final solution mixed 1:1 (v/v) with the final suspension of Bt sample (FS Bt sample) adjusted with purified water to a content of 0.4 mg/ml of total non-spore proteins of the *B. thuringi-*

*ensis* strain DSM 33173. FS Bt sample for DSM 33173 strain was not subjected to any purification process.

Formulation 3 (Bt DSM 33175): FBS final solution mixed 1:1 (v/v) with the final suspension of Bt sample (FS Bt sample) adjusted with purified water to a content of 0.4 mg/ml of total non-spore proteins of the *B. thuringiensis* strain DSM 33175. FS Bt sample for DSM 33175 did not contain parasporal crystal proteins.

Formulation 4 (DSM 33173, spore purified): Final suspension of Bt sample (FS Bt sample) for DSM 33173 strain was subjected to a further purification process in order to enrich the FS Bt sample with viable spores. For the purification step, the *B. thuringiensis* final suspension (FS Bt sample) was solubilized in a carbonate buffer solution at pH 9.0. After the solubilization, the suspension was centrifuged and the pellet re-suspended with Mili-Q water. The supernatant with the solubilized proteins was then discarded and the pellet was retained. The pellet was then adjusted with purified water to a content of 0.4 mg/ml of non-spore proteins of the *B. thuringiensis* strain DSM 33173. Finally, it was mixed with the FBS final solution at 1:1 (v/v) for the bioassay. Formulation 4 was rich in viable spores' content.

Formulation 5 (DSM 33173, heat-treated): FBS final solution mixed 1:1 (v/v) with a heat-treated final suspension of Bt sample (FS Bt sample), at 120° C. for minutes, and adjusted with purified water to a content of 0.4 mg/ml of total non-spore proteins of the *B. thuringiensis* strain DSM 33173. The heat-treatment performed on the FS Bt sample was carried out in order to inactivate both, non-spore proteins such as crystal proteins, and viable spores as well.

The coloring solution contained in the FBS final solution was used as an indicator to clearly identify those mites that had eaten any of the five experimental formulations.

*Dermanyssus gallinae*'s adults and nymphs samples were collected from a poultry (layers) farm with a high infestation rate of *Dermanyssus gallinae* mites. Healthy and moving mites were solely selected for this study. Mites were maintained in 50 ml-ventilated containers at 24-26° C. for one week without access to any source of food.

Mites were divided into 5 different groups of about 20 individuals each. Each group received one of the 5 different experimental formulations. Each group of mites was introduced into a methacrylate tube of approximately 10 cm of length and 0.5 cm of width. The methacrylate tube was sealed at one end by using a 20 µm mesh stuck with a 1 ml micropipette cut tip. At the other end, a 2×2 cm piece of one-day old chicken skin was held by a 1 ml micropipette tip containing 0.6 ml of the experimental formulations (1 to 5, one for each group).

Each group of mites was left at 30° C. and high relative humidity of 80-100% for 2 hours to freely ingest the experimental formulation. Later on, colored mites that had ingested the experimental formulations were selected. Colored mites were then introduced into new methacrylate tubes fully sealed at one end and with the other end sealed with a 20 µm mesh stuck with a 1 ml micropipette cut tip.

The activity of the five different experimental formulations was assessed by monitoring mortality of mites in each group. Mortality was checked at 24 hours by using an Stereo Microscope at 20-40×.

The mortality results are summarized in FIG. 1. The assay demonstrated that spores have a clear activity on mortality over *D. gallinae* mites, with respect to parasporal crystal proteins as the non-crystalliferous strain DSM 33175, that does not produce crystal protein at all, gave a mortality rate of 83% (Group 3) higher than formulations that contained both, spores and parasporal crystal proteins (67%, Group 2).

Furthermore, it was observed that the experimental formulation 4 which was enriched with purified viable spores (Group 4) resulted in an increase of activity over other formulations (in particular over formulation 2), causing a higher reduction of *D. gallinae* population (80% of mite mortality), when compared to non-purified formulation 2 that contained both, spores and parasporal crystals proteins (Group 2); the later resulting in 67% of mite mortality only.

In addition, when the viable spores and parasporal crystal proteins were subjected to an inactivation by heat-treatment, no mite mortality was observed (Group 5) at all.

Taking into account that the prior art clearly discloses that the toxic activity of *B. thuringiensis* strains used as insecticide in agriculture is due to the crystal proteins, these results are deemed surprising and unexpected because the inventors did not expect that a purified formulation enriched with viable spores had a better activity on mortality against mites than that observed in compositions containing crystal proteins.

Example 2: Spore Activity Assessment on Plate Bioassay

In order to demonstrate the activity of viable spores on mite mortality, a second assay was done. This time a new experimental model was used based on agar plate bioassay instead of the ingestion model used in Example 1. The plate bioassay better resembles future field conditions.

Different experimental formulations were prepared for the plate bioassay.

For this purpose, 7.5 g of European bacteriological agar were homogenized in 500 ml of Mili-Q water. The resulting homogenized agar was autoclaved at 121° C. for 20 minutes. 25 ml of the agar solution was then placed per plate (petri dish (such as Greiner bio-one petri dishes, ref. 633181, dish with lid, outside diameter of 93 mm, working volume of 15 ml, max. volume of 80 ml).

Three different experimental formulations were prepared as follows:

Formulation 1 (non-purified spore preparation): Final suspension of Bt sample (FS Bt sample) described in Example 1 was adjusted with purified water to a content about 2.5 mg/ml of non-spore proteins of *B. thuringiensis* strain DSM 33173.

Formulation 2 (purified spore preparation): Final suspension of Bt sample (FS Bt sample) described in Example 1 was subjected to a purification process in order to enrich the FS Bt sample with viable spores. For the purification step, the *B. thuringiensis* final suspension (FS Bt sample) was solubilized in a carbonate buffer solution at pH 9.0. After the solubilization, the suspension was centrifuged and the pellet resuspended with Mili-Q water. The supernatant was then discarded and the pellet was retained. The pellet was then adjusted with purified water to content about 2.5 mg/ml of non-spore proteins of the *B. thuringiensis* strain DSM 33173.

Formulation 3 (negative control): Mili-Q water was used as negative control.

µl/plate of each experimental formulation (1 to 3) described above was spared onto agar plates.

*Dermanyssus gallinae*'s adults and nymphs samples were collected from a poultry (layers) farm with a high infestation rate of *Dermanyssus gallinae* mites. Healthy and moving mites were only selected for the study. Mites were maintained in a 50 ml ventilated container at 24-26° C. for one week without access to any source of food. Mites were divided into 3 different groups of about 20 individuals each.

Each group of mites was placed onto an agar plate previously prepared with the experimental formulations (1 to 3) to be tested.

The petri dish was sealed using two face double-sided bonding tape in order to avoid mites to escape. The petri dish was kept at 26° C. and 70% Relative Humidity during the study. The activity of the three different experimental formulations was assessed by monitoring mortality of mites in each plate-group. Mortality was checked at 24 and 48 hours by using a Stereo Microscope at 20-40×.

Figure 2:
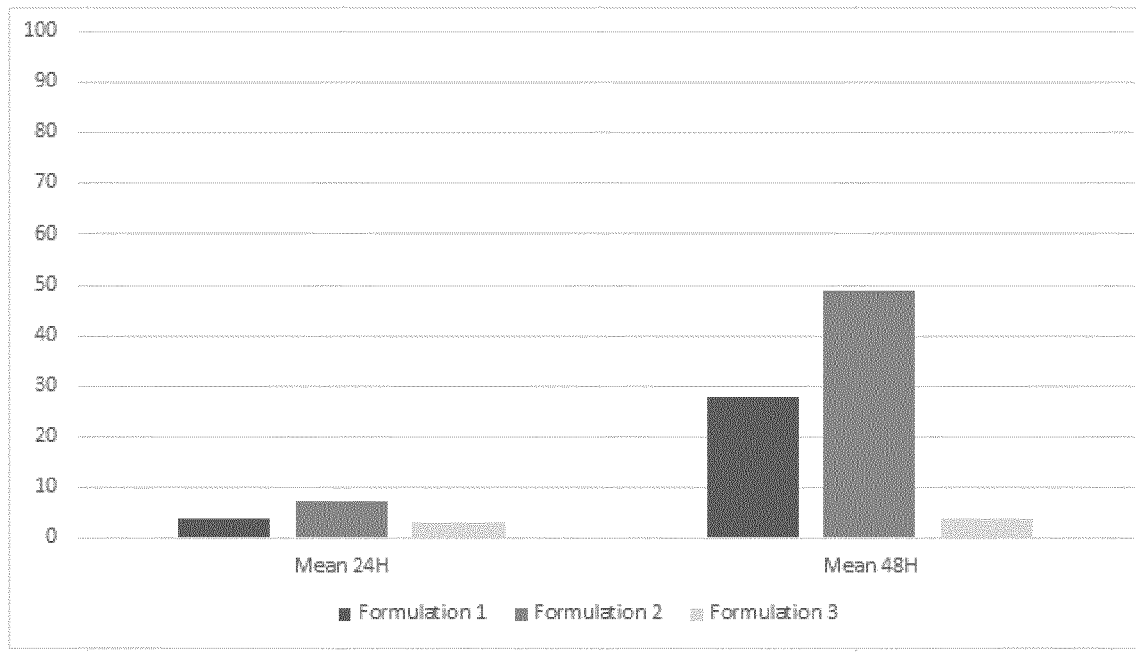

The mortality results are summarized in FIG. 2. The results obtained in Example 2 using a plate bioassay supported the effect observed in previous Example 1 using an ingestion bioassay experimental model.

The inventors consider the lower mortality percentages obtained in the Example 2, which is based on agar plate bioassay instead of the ingestion model used in Example 1, to be normal. Although, the plate bioassay better resembles future field conditions the mortality is always superior when the ingestion bioassay is used. This is because in the ingestion bioassay the mites ingest the experimental formulations, and only those mites having ingested the formulations are then selected for checking survival and mortality rates.

The plate bioassay demonstrated that formulation 2 based on purified spore preparation (Group 2) resulted in a higher mite mortality percentage than formulation 1 based on non-purified spore formulations (Group 1), where mortalities of 48.81% and 27.77% at 48 hours were obtained, respectively.

Once again, the inventors surprisingly found that compositions rich in parasporal crystal proteins performed worse than purified compositions rich in viable spores in terms of mortality rates against mites.

Example 3: Study on Dose-Response of Different Bt Compositions

This example was performed to check the activity of different *B. thuringiensis* (Bt) compositions comprising viable spores when different doses were used.

*Dermanyssus gallinae*'s adults and nymphs samples were collected from a poultry (layers) farm with a high infestation rate of *Dermanyssus gallinae* mites. Healthy and moving mites were selected for performing the dose/response assay. The assay was conducted using the model based on agar plate bioassay (Example 2) but using cell culture flasks (such as Falcon flask, ref. 353107, 12.5 cm$^2$, 25 ml, with vented screw cap) instead of petri dishes (such as Greiner bio-one petri dishes, ref. 633181, dish with lid, outside diameter of 93 mm, working volume of 15 ml, max. volume of 80 ml). The cell culture flasks were previously prepared with European bacteriological agar as described in Example 2. In this case, 11 ml of the agar solution was placed per flask instead of 25 ml per petri dish. Mites were collected from the farm and divided in nine different groups of about 20 individuals each.

The *B. thuringiensis* strains used in this study were GR-S5-8, an isolate which corresponds to a Bt strain isolated from a poultry farm located in Spain where a high infestation rate of *D. gallinae* was detected; GR-P14-3, an isolate which corresponds to a Bt strain isolated from a poultry farm located in Spain where a high infestation rate of *D. gallinae* was also detected; and DE2-S2-8, an isolate which corresponds to a Bt strain isolated from a poultry farm located in Germany where a low infestation rate of *D. gallinae* was detected. GR-S5-8 isolate corresponds to DSM 33175 strain which was deposited under the Budapest Treaty by HIPRA SCIENTIFIC, S.L.U. in the Leibnitz-Institut DSMZ-Deutsche Sammlung von Mikroorganismen und Zellkulturen on Jun. 20, 2019 as indicated above. DE2-S2-8 Bt isolate was also deposited under the Budapest Treaty by HIPRA SCIENTIFIC, S.L.U. in the Leibnitz-Institut DSMZ-Deutsche Sammlung von Mikroorganismen und Zellkulturen under the accession number DSM 33035, on Feb. 21, 2019.

All *B. thuringiensis* strains were grown as described in Example 1 to obtain the final suspension of Bt sample (FS Bt sample) for performing the dose-response assay. The number of viable spores per ml of the *B. thuringiensis* final suspension (FS Bt sample) was determined by standard microbiology techniques such as colony forming units (CFU)/ml.

As a side note, it is important to highlight that, as described above, the inventors decided to determine the number of viable spores per ml of the *B. thuringiensis* final suspension instead of determining or quantifying the concentration of the parasporal crystal proteins (non-spore proteins) in virtue of the results illustrated in examples 1 and 2 wherein the sought effect is linked to the spores and not to the parasporal crystal proteins.

The final suspension of Bt samples for strains GR-S5-8 and GR-P14-3 were then adjusted with purified water to 4 different fixed doses of viable spores/ml of preparation (CFU/ml). The four fixed doses of viable spores were $3.8 \times 10^7$, $1.1 \times 10^8$, $3.4 \times 10^8$, and $3.1 \times 10^9$ viable spores (CFU)/ml preparation. The different doses correspond to Groups 1 to 4 for GR-P14-3 strain and Groups 5 to 8 for the GR-S5-8 strain, respectively. On the other hand, the final suspension of the Bt sample for *B. thuringiensis* strain DE2-S2-8, was adjusted at a dose of $3.1 \times 10^9$ viable spores (CFU)/ml. This fixed dose corresponds to Group 9.

50 µl of the different Bt preparations adjusted to the different doses of viable spores/ml were introduced into the cell culture flasks. The flasks were kept at 26° C. and 70% Relative Humidity during the study. The activity of the different spores' preparations was assessed by monitoring mortality of mites in each flask. Mortality was checked at 24 and 48 hours by using a Stereo Microscope at 20-40×.

Figure 3:
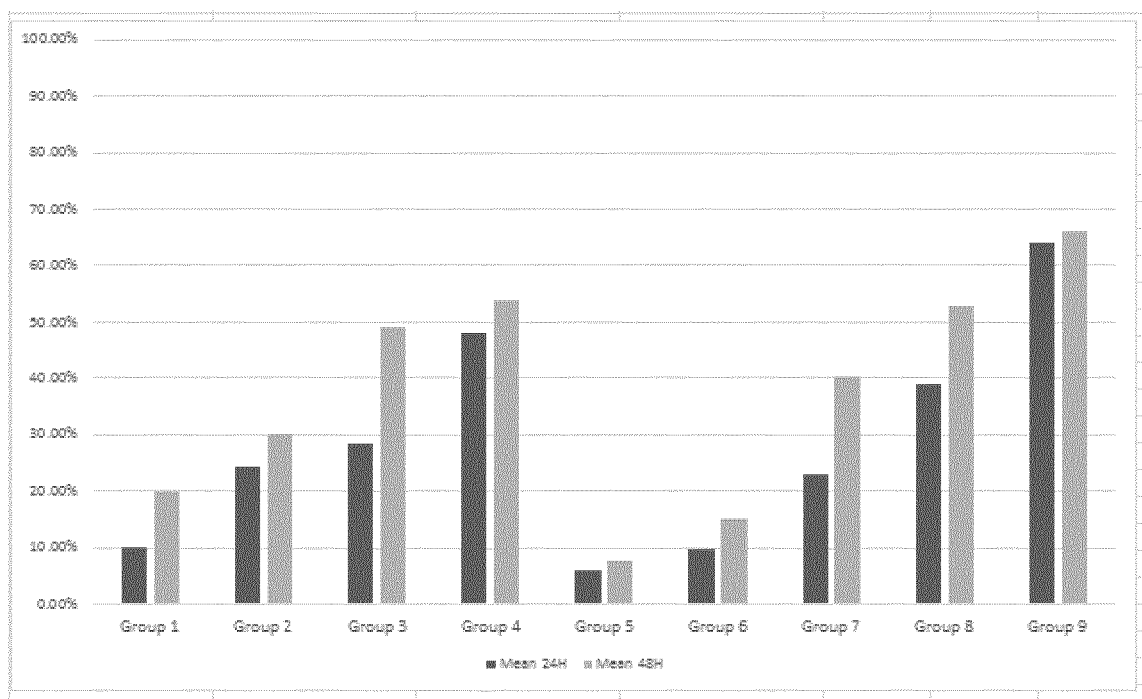

The results are summarized in the FIG. 3. The results demonstrated a clear role of the viable spores for producing anti-mite activity. It was observed that the lesser viable spores in the composition, the less mortality rate of *D. gallinae* mites was observed, both at 24 and 48 hours post-treatment with the experimental formulations. Likewise, the higher the dose of viable spores, the high mortality was also observed irrespective the content on non-spore proteins of the composition.

Furthermore, all the tested Bt strains had a significant mortality when formulated at $3.1 \times 10^9$ viable spores (CFU)/ml. In particular, the deposited DSM 33035 Bt strain, DE2-S2-8, demonstrated a higher degree of anti-mite activity, showing a mortality rate of 66% at 48 hours post-treatment (Group 9).

Example 4: Comparative Assay of the Activity of Different Bt Strains Against Mites In this example, we assessed the activity of different *B. thuringiensis* (Bt) strains isolated from poultry farms and compared to Bt strains isolated from commercial products used in agriculture against different kind of pests.

Seven different *B. thuringiensis* strains were included in the comparative assay; the Bt strains were:

DE2-S2-8 strain (isolated from a poultry farm with low *D. gallinae* infestation rate in Germany, DSM 33035), DE1-52-4 strain (isolated from a poultry farm with high *D. gallinae* infestation rate in Germany, DSM 33034), DE2-S1-1 strain (isolated from a poultry farm with low *D. gallinae* infestation rate in Germany), GR_P1_4 strain (isolated from a poultry farm with high *D. gallinae* infestation rate in Spain), MA_S15_3 strain (isolated from a poultry farm with low *D. gallinae* infestation rate in Spain), DE2-S3-4 strain (isolated from a poultry farm with low *D. gallinae* infestation rate in Germany), and

*B. thuringiensis* susbsp. kurstaki strain ABTS-351 (strain present in different commercial products from agriculture pests). In this case, it was isolated from the commercial product bioMAX 32®, manufactured by Valent BioScience LLC.

All seven Bt strains were cultured as described in Example 1 to obtain the final suspension of Bt sample (FS Bt sample) for performing the comparative assay. The number of viable spores per ml of the *B. thuringiensis* final suspension (FS Bt sample) was determined by standard microbiology techniques such as colony forming units (CFU)/ml (Goldman, E.; Green, L. H. Practical Handbook of Microbiology. 3$^{rd}$ Edition, published Jun. 4, 2015; Chapter 2. Quantification of Microorganisms. Page 19, Plate Count Method by Peter S. Lee, page 24. CRC Press, 1055 pages. ISBN 9781466587397). Counting colonies were performed manually using a pen and a click-counter.

*Dermanyssus gallinae*'s adults and nymphs samples were collected from a poultry (layers) farm with a high infestation rate of *Dermanyssus gallinae* mites. Healthy and moving mites were selected for performing the comparative assay. Mites were collected from the farm and divided into seven different groups of about 20 individuals each. The assay was conducted using the flask bioassay described in Example 3 (they were all previously prepared with European bacteriological agar as described in Example 2). 11 ml of the agar solution were placed per flask.

50 μl of a final suspension of Bt sample (FS Bt sample) prepared with each of the specific strain, was introduced into the cell culture flask of each group. The specific strains were grown as described in Example 1 and adjusted with purified water to a content of $3.1 \times 10^9$ viable spores (CFU)/ml preparation. The non-spore protein content was further determined as described in Example 1.

The flasks were kept at 26° C. and 70% Relative Humidity during the study. The activity of the different spores preparations was assessed by monitoring mortality of mites in each flask. Mortality was checked at 24 and 48 hours by using a Stereo Microscope at 20-40×.

The results of mortality are summarized in the table 1.

TABLE 1

| *B. thuringiensis* strain | Mite mortality at 48 h | Content on Non-spore protein |
|---|---|---|
| DE2-S2-8 | 58.94% | 0.270 mg/ml |
| DE1-S2-4 | 56.79% | 0.529 mg/ml |
| DE2-S1-1 | 53.77% | 0.390 mg/ml |
| GR_P1_4 | 51.92% | 0.220 mg/ml |
| MA_S15_3 | 51.30% | 0.210 mg/ml |
| DE2-S3-4 | 48.64% | 0.750 mg/ml |
| ABTS-351 | 24.68% | 1.758 mg/ml |

All preparations resulted in mite mortality at 48 hours. However, the mortality against mites, such as *Dermanyssus gallinae*, observed from the Bt commercial product used for controlling agricultural pests was significantly reduced when using the preparation containing the *B. thuringiensis* subsp. kurstaki strain ABTS-351, present as said in common agriculture commercial products. On the contrary, Bt strains other than commercial Bt subsp. kurstaki doubled the activity on mortality against mites. Other preparations tested having a high non-spore protein content, such as *B. thuringiensis* subsp. aizawai (3.09 mg/ml; 21.33% mortality), *B. thuringiensis* subsp. morrisoni (1.24 mg/ml; 22.50% mortality), or *B. thuringiensis* subsp. israelensis (0.91 mg/ml; 30.36% mortality), further demonstrated the above mentioned relationship with the activity on mortality against mites.

Therefore, surprisingly, it was observed that in general the Bt strains resulting in high mortality rates against mites were those that produced lower amount of non-spore proteins with respect to the viable spores contained in the preparations. The higher the content on non-spore proteins the less activity observed.

Example 5: Activity of Bt Compositions Comprising Mineral Oil

In this example, the activity of *B. thuringiensis* compositions comprising mineral oil was assessed. For the study, a suspension of Bt sample (FS Bt sample) based on Bt strain DE2-S2-8 (DSM 33035) as described in Example 1 was prepared. Subsequently, six different formulations containing different amounts of viable spores/ml and formulated with and without mineral oil were prepared as follows:

Formulation 1. FS Bt sample of DE2-S2-8 strain was mixed with 86.2% (v/v) of a PBS emulsion containing 20% (v/v) of mineral oil (Marcol 52), 0.9% of Polysorbate 80, 0.65% of Sorbitan monooleate, and 2.4% of Simulsol 5100. The final content of the sample was adjusted to $3.4 \times 10^8$ viable spores (CFU)/ml.

Formulation 2. FS Bt sample of DE2-S2-8 strain was mixed with 86.2% (v/v) of a PBS emulsion containing 20% (v/v) of mineral oil (Marcol 52), 0.9% of Polysorbate 80, 0.65% of Sorbitan monooleate, and 2.4% of Simulsol 5100. The final content of the sample was adjusted to $1.03 \times 10^9$ viable spores (CFU)/ml.

Formulation 3. FS Bt sample of DE2-S2-8 strain was mixed with 86.2% (v/v) of a PBS emulsion containing 20% (v/v) of mineral oil (Marcol 52), 0.9% of Polysorbate 80, 0.65% of Sorbitan monooleate, and 2.4% of Simulsol 5100. The final content of the sample was adjusted to a content of $3.10 \times 10^9$ viable spores (CFU)/ml.

Formulation 4. FS Bt sample of DE2-S2-8 strain adjusted with purified water to a content of $1.03 \times 10^9$ viable spores (CFU)/ml.

Formulation 5. FS Bt sample of DE2-S2-8 strain adjusted with purified water to a content of $3.10 \times 10^9$ viable spores (CFU)/ml.

Formulation 6. Negative control, of Mili-Q water was used.

*Dermanyssus gallinae*'s adults and nymphs samples were collected from a poultry (layers) farm with a high infestation rate of *Dermanyssus gallinae* mites. Healthy and moving mites were selected for performing the assay. Mites were collected from the farm and divided into 6 different groups of about 20 individuals each. The assay was conducted using the flask bioassay described in Example 3 (they were all previously prepared with European bacteriological agar as described in Example 2). 11 ml of the agar solution were placed per flask.

50 µl of a final suspension of Bt sample (FS Bt sample) prepared with each formulation (1 to 5) was introduced into the cell culture flask of each group. Group 6 received 50 µl of Mili-Q water as a negative control. The flasks were kept at 26° C. and 70% Relative Humidity during the study. The activity of the different formulations was assessed by monitoring mortality of mites in each flask. Mortality was checked at 24 and 48 hours by using a Stereo Microscope at 20-40×.

Figure 4:
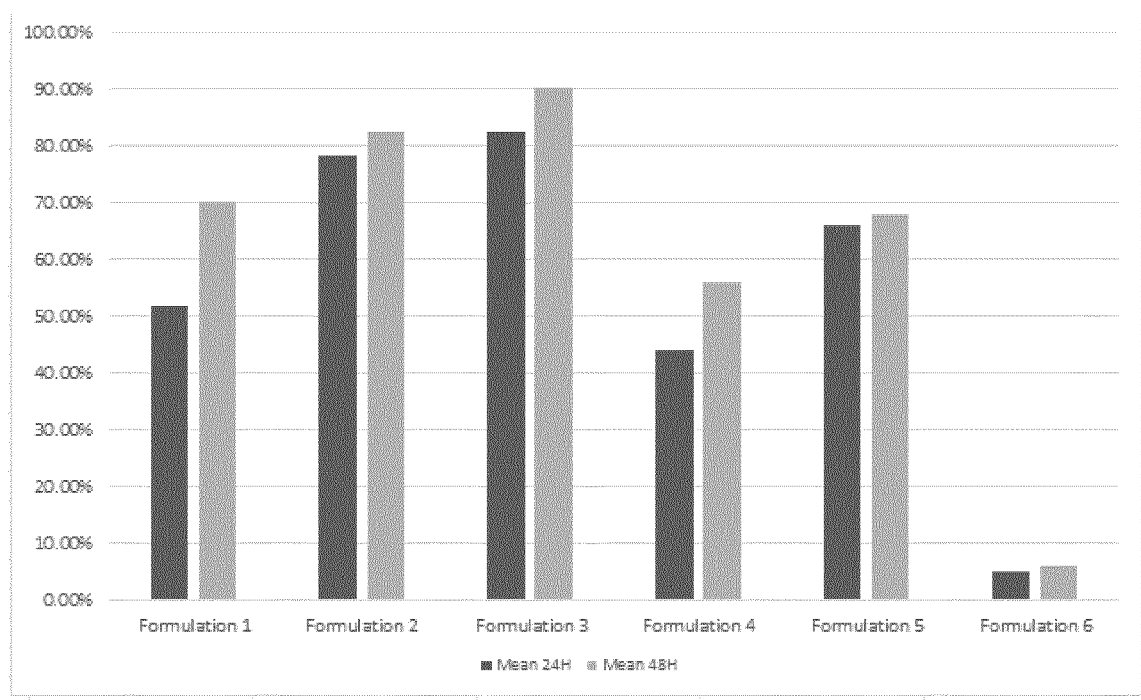

The results of mortality are summarized in FIG. 4. Unexpectedly, the mixture of the *B. thuringiensis* preparations with mineral oil did not have a negative impact on the viability of *B. thuringiensis* strains and their anti-mite activity. On the contrary, it considerably increased the effect of the experimental formulations resulting in a synergic effect on mite mortality. Formulation 3 prepared with mineral oil and $3.1 \times 10^9$ viable spores (CFU)/ml (Group 3) achieved an exceptional mite mortality rate over 90% in just 48 hours.

It was further observed that the mixture of the *B. thuringiensis* formulations blended in mineral oil preparations, allowed reducing the dose of *B. thuringiensis* bacteria used in the experimental formulations. For instance, mineral oil preparation formulated with a dose of $3.4 \times 10^8$ viable spores (CFU)/ml (Group 1) resulted in a mite mortality rate of 70.10% at 48 hours. Similar mortality rate was obtained when the *B. thuringiensis* formulation was not mixed with mineral oil but in this case it was formulated at a dose of $3.1 \times 10^9$ viable spores (CFU)/ml (Group 5), i.e. much higher dose was needed to achieve a similar result on mortality rate (68%) without the presence of mineral oil in the experimental formulations.

Thus, the synergistic effect of Bt preparations plus mineral oil was confirmed by the inventors. In additional experiments, it was also observed that mixing the FS Bt sample with an emulsion comprising very low percentages of mineral oil, such as 1.25% a synergistic effect was still maintained.

CLAUSES

1. A pharmaceutical or biocide composition suitable for controlling or reducing mite infestations, comprising as an active ingredient a bacterial preparation of at least one strain of *Bacillus thuringiensis* (*B. thuringiensis*), characterized in that the bacterial preparation comprises an effective amount of viable spores of at least said one strain of *B. thuringiensis*.
2. The pharmaceutical or biocide composition of clause 1, wherein the bacterial preparation comprises an effective amount of viable spores of at least one strain of *B. thuringiensis* suitable for controlling or reducing mite infestations produced by *Dermanyssus gallinae* (poultry red mite).
3. The pharmaceutical or biocide composition of clause 1 or 2, wherein the at least one strain of *B. thuringiensis* is a strain that produces less amount of *B. thuringiensis* non-spore proteins such as parasporal crystal proteins than *B. thuringiensis* subsp. Kurstaki, subsp. Aizawi, subsp. Israelensis, subsp. Morrisoni.
4. The pharmaceutical or biocide composition of clause 1 or 2, wherein the at least one strain of *B. thuringiensis* is a strain that produces less than 1.7 mg/ml of *B. thuringiensis* non-spore proteins such as parasporal crystal proteins for every $3.1 \times 10^9$ viable spores per ml.
5. The pharmaceutical or biocide composition of clause 3 or 4, wherein the *B. thuringiensis* non-spore proteins are selected from the list consisting of delta (5)-endotoxins, proteins Cry and Cyt, vegetative insecticidal proteins (Vip1, Vip2, Vip3 and Vip4), secreted insecticidal proteins (Sip proteins), β-exotoxins (thuringiensin), proteins related to cholesterol-dependent cytolysins (sphaericolysins and alveolysins), Enhancing-like proteins (Bel enhancing protein), Helper proteins (P19 and P20 proteins), or non-proteinaceous β-exotoxin (Bt 41.9-kDa protein).
6. The pharmaceutical or biocide composition according to any one of clauses 1 to 5, wherein the bacterial preparation comprises an effective amount of at least $1 \times 10^4$ cfu of viable spores per ml of the composition.
7. The pharmaceutical or biocide composition according to clause 6, wherein the bacterial preparation comprises an effective amount of at least $3 \times 10^8$ cfu of viable spores per ml of the composition.
8. The pharmaceutical or biocide composition according to clause 6, wherein the bacterial preparation comprises an effective amount of at least $3 \times 10^9$ cfu of viable spores per ml of the composition.
9. The pharmaceutical or biocide composition according to any one of clauses 1 to 8, further comprising at least one further active or functional ingredient selected from the group consisting of an insecticide, an acaricide, a fungicide, a nematicide, an antibiotic, a cleaning agent, an immunogenic agent, animal feedstuff, an essential oil, a mineral oil, a nutraceutical, a probiotic, a prebiotic, a symbiotic, a polysaccharide, and combinations thereof.
10. The pharmaceutical or biocide composition according to clause 9, wherein the further active ingredient is an immunogenic agent derived from a microorganism selected from the group consisting of IBv, NDV, Adenovirus, EDS, IBDV, chicken anemia virus, avian encephalo-myelitis virus, fowl pox virus, turkey rhinotracheitis virus, duck plague virus, pigeon pox virus, MDV, avian leucosis virus, ILTV, avian pneumovirus, reovirus, *Escherichia coli*, *Salmonella* sp., *Ornithobacterium rhinotracheale*, *Haemophilus paragallinarum*, *Pasteurella multocida*, *Erysipelothrix rhusiopathiae*, *Erysipela* sp., *Mycoplasma* sp., *Clostridium* sp., *Eimeria* sp., and *Aspergillus* sp.
11. The pharmaceutical or biocide composition according to any one of clauses 1 to 10, wherein the composition is in the form selected from the group consisting of dust, powder, granular formulation, microencapsulated formulation, lotion, ointment, gel, cream, paste, suspension, liquid concentrate, solution and emulsion.
12. The pharmaceutical or biocide composition according to any one of clauses 1 to 11, wherein the composition is suitable for application by bathing, spraying, pouring, painting, jetting, dipping or dusting.
13. The pharmaceutical or biocide composition according to any one of clauses 1 to 12, wherein the composition further comprises one or more pharmaceutically acceptable vehicles and/or one or more acceptable adjuvants.
14. The pharmaceutical or biocide composition according to any of clauses 1 to 13, wherein the at least one strain of *Bacillus thuringiensis*, is the *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33034 on Feb. 21, 2019, respectively, and mutants thereof.

15. The pharmaceutical or biocide composition according to any of clauses 1 to 13, wherein the at least one strain of *Bacillus thuringiensis*, is the *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33035 on Feb. 21, 2019, respectively, and mutants thereof.

16. The pharmaceutical or biocide composition according to any of clauses 1 to 13, wherein the at least one strain of *Bacillus thuringiensis* is the *Bacillus thuringiensis* (Bt) strain GR-S5-8 deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen and Zellkulturen (Inhoffenstraße 7B, 38124 Braunschweig, Germany) under the accession numbers DSM 33175 on Jun. 20, 2019, respectively, and mutants thereof.

17. The pharmaceutical or biocide composition as defined in any of clauses 1 to 16, for use as a medicament or as a biocide.

18. The pharmaceutical or biocide composition as defined in any of clauses 1 to 16, for use in the control and/or reduction of mite infestations.

19. The pharmaceutical or biocide composition as defined in any of clause 1 to 16, for use in the prevention and/or treatment of a disease caused by ectoparasite mites in an animal in need thereof.

20. The pharmaceutical or biocide composition for use according to clause 19, wherein the disease is caused by an ectoparasite mite selected from the group consisting of *Dermanyssus* sp., *Ornithonyssus* sp., *Argus* sp., Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus minor, Otodectes *cynotis, Cheyletiella yasguri, Demodex* sp., Notoederes *cati*, Cheyletella sp., *Psoroptes* sp., Chorioptes sp., Psorergates *ovis, Sarcoptes scabiei, Psorobia ovis*, Raillietia *auris* and *Varroa* sp., and combinations thereof.

21. The pharmaceutical or biocide composition as defined in any of clauses 1 to 16, for use in the control and/or reduction of mite infestations produced by ectoparasite mites, preferably in animals or fomites.

22. The pharmaceutical or biocide composition for use according to clause 21, wherein the ectoparasite mite is selected from the group consisting of *Dermanyssus* sp, *Ornithonyssus* sp, *Argus* sp, Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus minor, Otodectes *cynotis, Cheyletiella yasguri, Demodex* sp., Notoederes *cati, Cheyletiella* sp., *Psoroptes* sp., Chorioptes sp., Psorergates *ovis, Sarcoptes scabiei, Psorobia ovis*, Raillietia *auris* and *Varroa* sp., and combinations thereof.

23. The pharmaceutical or biocide composition for use according to clause 20 or 22, wherein the ectoparasite mite is *Dermanyssus gallinae* (poultry red mite).

24. The pharmaceutical or biocide composition for use according to any of clauses 18 or 21 to 23, wherein the control and/or reduction of mite infestation results in a mortality rate of at least 25% of the mites.

25. The pharmaceutical or biocide composition for use according to clause 24, wherein the mortality rate of at least 25% of the mites results in 48 hours from the moment in which the composition has been applied onto and/or has contacted with said mites.

26. The pharmaceutical or biocide composition for use according to any of clauses 17 to 25, wherein the composition is applied by bathing, spraying, pouring, painting, jetting, dipping or dusting.

27. The pharmaceutical or biocide composition for use according to any of clauses 17 to 26, wherein the at least one strain of *Bacillus thuringiensis*, is the *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33034 on Feb. 21, 2019, respectively, and mutants thereof.

28. The pharmaceutical or biocide composition for use according to any of clauses 17 to 26, wherein the at least one strain of *Bacillus thuringiensis*, is the *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession numbers DSM 33035 on Feb. 21, 2019, respectively, and mutants thereof.

29. The pharmaceutical or biocide composition for use according to any of clauses 17 to 26, wherein the at least one strain of *Bacillus thuringiensis* is the *Bacillus thuringiensis* (Bt) strain GR-S5-8 deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen and Zellkulturen (Inhoffenstraße 7B, 38124 Braunschweig, Germany) under the accession numbers DSM 33175 on Jun. 20, 2019, respectively, and mutants thereof.

30. The pharmaceutical or biocide composition for use according to any one of clauses 19 to 29, wherein the animals are selected from the group consisting of avian, porcine, bovine, equine, feline, canine, ovine, rabbit and honeybees species.

31. The pharmaceutical or biocide composition for use according to clause 30, wherein the avian species are poultry.

32. A method for the control and/or reduction of mite infestations in fomites, wherein the method comprises using the composition as defined in any one of clauses 1 to 16.

33. The method according to clause 32, wherein the control and/or reduction of mite infestation results in mortality rate of at least 25% of the mites.

34. The method according to clause 33, wherein the mortality rate of at least 25% of the mites results in 48 hours from the moment in which the composition has been applied onto and/or contacted with said mites and/or fomites.

35. The method according to any of clauses 32 to 34, wherein the composition has been applied by bathing, spraying, pouring, painting, jetting, dipping or dusting.

36. The method according to any one of clauses 32 to 35, wherein the fomites are located in premises where the animals are kept.
37. The pharmaceutical or biocide composition according to any of clauses 1 to 16, wherein the composition comprises a further active ingredient and said further active ingredient is an essential oil or a mineral oil.
38. The pharmaceutical or biocide composition of clause 37, wherein said composition is formulated in said essential oil or mineral oil.
39. The pharmaceutical or biocide composition according to any of clauses 37 to 38, wherein the further active ingredient is a mineral oil, preferably said mineral oil is liquid paraffin.
40. The pharmaceutical or biocide composition according to any of clauses 37 to 39, for use in the control and/or reduction of mite infestations, preferably in animals or fomites.
41. The pharmaceutical or biocide composition according to any of clauses 37 to 40, wherein the at least one strain is selected so that the control and/or reduction of mite infestation results in mortality rate of at least 50% of the mites.
42. The pharmaceutical or biocide composition according to clause 41, wherein the mortality rate of at least 50% of the mites results in 48 hours from the moment in which the composition has been applied onto and/or contacted with said mites and/or fomites.
43. The pharmaceutical or biocide composition for use according to any of clauses 41 to 42, wherein the mortality rate of at least 50% of the mites, preferably in 48 hours from the moment in which the composition has been applied onto said mites or fomites, is performed by bathing, spraying, pouring, painting, jetting, dipping or dusting.
44. The pharmaceutical or biocide composition or the pharmaceutical or biocide composition for use according to any of clauses 37 to 43, wherein the mite is an ectoparasite mite.
45. The pharmaceutical or biocide composition or the pharmaceutical or biocide composition for use according to clause 44, wherein the ectoparasite mite is selected from the group consisting of *Dermanyssus* sp, *Ornithonyssus* sp, *Argus* sp, Allopsoroptoides galli, Neocnemidocoptes gallinae, *Knemidocoptes mutans*, Laminosioptes cysticola, Megninia cubitalis, Megninia ginglymura, Pterolichus obtus, Syringophilus bipectinatus, Columbiphilus polonica, Deroglyphus elongates, Gaudoglyphus minor, Otodectes *cynotis, Cheyletiella yasguri, Demodex* sp., Notoederes *cati, Cheyletiella* sp., *Psoroptes* sp., Chorioptes sp., Psorergates *ovis, Sarcoptes scabiei, Psorobia ovis*, Raillietia *auris* and *Varroa* sp., and combinations thereof.
46. The pharmaceutical or biocide composition or the pharmaceutical or biocide composition for use according to clause 45, wherein the ectoparasite mite is *Dermanyssus gallinae* (poultry red mite).
47. The pharmaceutical or biocide composition or the pharmaceutical or biocide composition for use according to any of clauses 37 to 46, wherein the control and/or reduction of mite infestations is performed in animals selected from the group consisting of avian, porcine, bovine, equine, feline, canine, ovine, rabbit and honeybees species.
48. The pharmaceutical or biocide composition or the pharmaceutical or biocide composition for use according to clause 47, wherein the avian species are poultry.
49. The pharmaceutical or biocide composition or the pharmaceutical or biocide composition for use according to any of clauses 37 to 48, wherein the composition is suitable for application by bathing, spraying, pouring, painting, jetting, dipping or dusting.
50. The pharmaceutical or biocide composition or the pharmaceutical or biocide composition for use according to any of clauses 37 to 49, wherein the composition is suitable for application by spraying.
51. The pharmaceutical or biocide composition or the pharmaceutical or biocide composition for use according to any of clauses 37 to 50, wherein the control and/or reduction of mite infestations is performed in fomites, wherein the fomites are located in premises where the animals are kept.

The invention claimed is:

1. A pharmaceutical or biocide composition suitable for controlling or reducing mite infestations, comprising as an active ingredient a bacterial isolate of at least one strain of *Bacillus thuringiensis* (*B. thuringiensis*), wherein the bacterial isolate comprises an effective amount of viable spores of at least said one strain of *B. thuringiensis*; and wherein:
   (a) the at least one strain of *B. thuringiensis* is a strain that produces less than 1.7 mg/ml of *B. thuringiensis*' non-spore proteins for every $3.1 \times 10^9$ viable spores per ml; and
   (b) the pharmaceutical or biocide composition is in a pharmaceutical form selected from the group consisting of: dust, powder, granular formulation, microencapsulated formulation, lotion, ointment, gel, cream, paste, suspension, liquid concentrate, solution and emulsion.

2. The pharmaceutical or biocide composition of claim 1, wherein the bacterial isolate comprises an effective amount of viable spores of at least one strain of *B. thuringiensis* suitable for controlling or reducing mite infestations produced by *Dermanyssus gallinae* (poultry red mite).

3. The pharmaceutical or biocide composition of claim 1, wherein the *B. thuringiensis*' non-spore proteins are selected from the group consisting of delta (δ)-endotoxins, proteins Cry and Cyt, vegetative insecticidal proteins (Vip1, Vip2, Vip3 and Vip4), secreted insecticidal proteins (Sip proteins), β-exotoxins (thuringiensin), proteins related to cholesterol-dependent cytolysins (sphaericolysins and alveolysins), Enhancing-like proteins (Bel enhancing protein), Helper proteins (P19 and P20 proteins), and non-proteinaceous β-exotoxin (Bt 41.9-kDa protein).

4. The pharmaceutical or biocide composition according to claim 1, wherein the bacterial isolate comprises an effective amount of at least $1 \times 10^4$ cfu of viable spores per ml of the composition.

5. The pharmaceutical or biocide composition according to claim 1, further comprising at least one further active or functional ingredient selected from the group consisting of an insecticide, an acaricide, a fungicide, a nematicide, an antibiotic, a cleaning agent, an immunogenic agent, animal feedstuff, an essential oil, a mineral oil, a nutraceutical, a probiotic, a prebiotic, a symbiotic, a polysaccharide, and combinations thereof.

6. The pharmaceutical or biocide composition according to claim 5, wherein the further active ingredient is a mineral oil, and said mineral oil is liquid paraffin.

7. The pharmaceutical or biocide composition according to claim 1, wherein the at least one strain of *Bacillus thuringiensis*, is selected from the group consisting of:
   a. the *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession number DSM 33034 on Feb. 21, 2019, respectively;

b. the *B. thuringiensis* strain deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession number DSM 33035 on Feb. 21, 2019, respectively;

and c. the *Bacillus thuringiensis* (Bt) strain GR-S5-8 deposited under the Budapest Treaty by HIPRA SCIENTFIC, S.L.U. (Avda de La Selva 135, 17170 Amer, Girona, Spain) in the Leibnitz-Institut DSMZ-Deutsche Sammlung von Mikroorganismen und Zellkulturen (Inhoffenstraße 7B, 38124 Braunschweig, Germany) under the accession number DSM 33175 on Jun. 20, 2019, respectively.

8. A method for controlling and/or reducing ectoparasite mite infestations, comprising applying the pharmaceutical or biocide composition as defined in claim 1 to an animal or fomite in need thereof.

9. A method for prevention and/or treatment of a disease caused by ectoparasite mites in an animal in need thereof, comprising administering the pharmaceutical or biocide composition as defined in claim 1 to an animal in need thereof.

10. The method according to claim 8, wherein the ectoparasite mite is selected from the group consisting of *Dermanyssus* sp, *Ornithonyssus* sp, *Argus* sp, Allopsoroptoides galli, Neocnemidocoptes *gallinae, Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus minor, Otodectes *cynotis, Cheyletiella yasguri, Demodex* sp., Notoederes *cati, Cheyletiella* sp., *Psoroptes* sp., Chorioptes sp., Psorergates *ovis, Sarcoptes scabiei, Psorobia ovis*, Raillietia *auris* and *Varroa* sp. and combinations thereof.

11. The method according to claim 10, wherein the ectoparasite mite is *Dermanyssus gallinae* (poultry red mite).

12. The pharmaceutical or biocide composition of claim 1, wherein the composition further comprises a pharmaceutically acceptable vehicle and/or an acceptable adjuvant.

13. The method according to claim 8, wherein the composition is applied by bathing, spraying, pouring, painting, jetting, dipping or dusting.

14. The method according to claim 8, wherein the composition is applied to animals selected from avian, porcine, bovine, equine, feline, canine, ovine, rabbit and honeybee species.

15. The method according to claim 8, wherein the control and/or reduction of mite infestation results in a mortality rate of at least 25% of the mites.

16. The method according to claim 15, wherein the mortality rate of at least 25% of the mites results in 48 hours from the moment in which the composition has been applied onto and/or has contacted with said mites.

17. A method for the control and/or reduction of mite infestations in fomites, wherein the method comprises applying the composition as defined in claim 1 to a fomite in need thereof.

18. The method according to claim 9, wherein the ectoparasite mite is selected from the group consisting of *Dermanyssus* sp, *Ornithonyssus* sp, *Argus* sp, Allopsoroptoides galli, Neocnemidocoptes *gallinae, Knemidocoptes mutans*, Laminosioptes cysticola, Megninia cubitalis, Megninia ginglymura, Pterolichus obtus, Syringophilus bipectinatus, Columbiphilus *polonica*, Deroglyphus elongates, Gaudoglyphus minor, Otodectes *cynotis, Cheyletiella yasguri, Demodex* sp., Notoederes *cati, Cheyletiella* sp., *Psoroptes* sp., Chorioptes sp., Psorergates *ovis, Sarcoptes scabiei, Psorobia ovis*, Raillietia *auris* and *Varroa* sp. and combinations thereof.

19. The method according to claim 18, wherein the ectoparasite mite is *Dermanyssus gallinae* (poultry red mite).

20. The method according to claim 9, wherein the composition is applied by bathing, spraying, pouring, painting, jetting, dipping or dusting.

21. The method according to claim 9, wherein the composition is applied to animals selected from avian, porcine, bovine, equine, feline, canine, ovine, rabbit and honeybee species.

* * * * *

UNITED STATES PATENT AND TRADEMARK OFFICE
CERTIFICATE OF CORRECTION

PATENT NO. : 12,290,537 B2
APPLICATION NO. : 17/630450
DATED : May 6, 2025
INVENTOR(S) : Marc Pagès Bosch et al.

Page 1 of 1

It is certified that error appears in the above-identified patent and that said Letters Patent is hereby corrected as shown below:

In the Specification

Column 12, Line 61:
"delta (8)-endotoxins," should read: --delta (δ)-endotoxins,--.

Column 28, Line 3:
"delta (5)-endotoxins," should read: --delta (δ)-endotoxins,--.

In the Claims

Column 32, Claim 3, Line 40:
"delta (8)-endotoxins," should read: --delta (δ)-endotoxins,--.

Signed and Sealed this
Twenty-second Day of July, 2025

Coke Morgan Stewart
*Acting Director of the United States Patent and Trademark Office*